United States Patent [19]

Harris et al.

[11] Patent Number: 5,691,175

[45] Date of Patent: Nov. 25, 1997

[54] IMMORTALIZED HUMAN FETAL OSTEOBLASTIC CELLS

[75] Inventors: Steven A. Harris; Thomas C. Spelsberg, both of Rochester, Minn.

[73] Assignee: Mayo Foundation for Medical Education and Research, Rochester, Minn.

[21] Appl. No.: 89,848

[22] Filed: Jul. 12, 1993

[51] Int. Cl.$^6$ .............................. C12N 15/64; C12N 5/10
[52] U.S. Cl. ..................................... 435/172.3; 435/240.2
[58] Field of Search ........................... 435/240.2, 172.3

[56] References Cited

U.S. PATENT DOCUMENTS 5,028,425  7/1991  Good et al. ...................... 424/191.1

OTHER PUBLICATIONS

Price et al., *Eur. J. Clin. Nutr.*, vol. 48, Suppl. 1, 1994, pp. S131–S149.
Pfeilschifter et al., *Endocrinology*, vol. 127, 1990, pp. 69–75.
Quarles, *Miner. Electrolyte Metab.*, vol. 17, 1991, pp. 233–239.
Bodo et al., *Cell. Mol. Biol.*, vol. 37, 1991, pp. 597–606.
T.K. Gray et al., "Estradiol Stimulates in vitro the Secretion of Insulin–like Growth Factors by the Clonal Osteoblastic Cell Line, UMR106", *Bioc. Biophys. Res. Comm.*, 158, 407–412 (1989).
P.J. Greenaway et al., "Human cytomegalovirus DNA: BamHi, EcoRI and PstI restriction endonuclease cleavage maps", *Gene*, 18, 355–360 (1982).
R.G. Ham et al., "Media and Growth Requirements", *Methods Enzymol.*, 58, 44–93 (1979).
S.A. Harris et al., "Estrogen Induces C–FOS Promoter Activity in Normal Human Osteoblast–Like Cells", *J. Bone Min. Res.*, 7, Abstract No. 7 (1992).
S.A. Harris et al., "Development and Characterization of a Conditionally Immortilized Human Fetal Osteoblastic Cell Line", *J. Bone Min. Res.*, 1–14 (1993).
S.A. Harris et al., "Development and Characterization of a Conditionally–Transformed Human Fetal Osteoblastic Cell Line", *J. Bone Min. Res.*, 8, S303, Abstract No. 745 (1993).
R.L. Jilka et al., "Increased Osteoclast Development After Estrogen Loss: Mediation by Interleukin–6", *Science*, 257, 88–91 (Jul. 3, 1992).
K.J. Kaneko et al., "Activation of the Silent Progesterone Receptor Gene by Ectopic Expression of Estrogen Receptors in a Rat Fibroblast Cell Line", *Biochemistry*, 32, 8348–8359 (1993).
B.S. Komm, "Estrogen Binding, Receptor mRNA, and Biologic Response in Osteoblast–Like Osteosarcoma Cells", *Science*, 241, 81–84 (Jul. 1, 1988).
Y. Liel et al, "Evidence That Estrogens Modulate Activity and Increase the Number of 1,25–Dihydroxyvitamin D Receptors in Osteoblast–Like Cells (ROS 17/2.8)", *Endocrinology*, 130, 2597–2601 (1992).

R. Lindsay, "The influence of cigarette smoking on bone mass and bone loss", *Osteoporosis: Recent Advances in Pathogenesis and Treatment;* University Park Press: Baltimore, MD; 481 (1981).
A.M. Maxam et al., "Sequencing End–Labeled DNA with Base–Specific Chemical Cleavages", *Methods Enzymol.*, 65, 499–560 (1980).
G.K. McMaster et al, "Analysis of single–and double–stranded nucleic acids on polyacrylamide and agarose gels by using glyoxal and acridine orange", *Proc. Natl. Acad. Sci. USA*, 74, 4835–4838 (Nov. 1977).
J. Messing et al., "A system for shotgun DNA sequencing", *Nucl. Acids Res.*, 9, 309–320 (1981).
R.C. Mulligan et al., "Expression of a Bacterial Gene in Mammalian Cells", *Science*, 209, 1422–1427 (1980).
M.J. Oursler et al, "Modulation of Transforming Growth Factor–$\beta$ Production in Normal Human Osteoblast–Like Cells by 17$\beta$–Estradiol and Parathyroid Hormone", *Endocrinology*, 129, 3313–3320 (1991).
R. Pacifici et al., "Ovarian steroid treatment blocks a postmenopausal increase in blood monocyte interleukin 1 release", *Proc. Natl. Acad. Sci. USA*, 86, 2398–2402 (Apr. 1989).
G. Passeri et al., "Increased Interleukin–6 Production by Murine Bone Marrow and Bone Cells after Estrogen Withdrawal", *Endocrinology*, 133, 822–828 (1993).
G.N. Pavlakis et al., "Expression of two human growth hormone genes in monkey cells infected by simian virus 40 recombinants", *Proc. Natl. Acad. Sci. USA*, 7, 7398–7402 (Dec. 1981).
B.L. Riggs et al., "Short–and Long–Term Effects of Estrogen and Synthetic Anabolic Hormone in Postmenopausal Osteoporosis", *J. Clin. Investigation*, 51, (Jul. 1972).
P. Sassone–Corsi et al., "Transcriptional autoregulation of the proto–oncogene fos", *Nature*, 334, 314–319 (Jul. 1988).
B. Sugden et al., "A Vector That Replicates as a Plasmid and Can be Efficiently Selected in B–Lymphoblasts Transformed by Epstein–Barr Virus" *Mol. Cell. Biol.*, 5, 410–413 (Feb. 1985).
S.N. Thibodeau et al., "Simultaneous Measurement of Estrogen and Progesterone Receptors in Tumor Cytosols with Use of $^{125}$I–Labeled Estradiol and of $^3$H–R5020", *Clin. Chem.*, 27, 687–691 (1981).
D.R. Thomsen, "Promoter–regulatory region of the major immediate early gene of human cytomegalovirus", *Proc. Natl. Acad. Sci. USA*, 81, 659–663 (Feb. 1984).
L. Tora et al., "The cloned human oestrogen receptor contains a mutation which alters its hormone binding properties", *EMBO J.*, 8, 1981–1986 (1989).

(List continued on next page.)

*Primary Examiner*—Mindy Fleisher
*Assistant Examiner*—James Ketter
*Attorney, Agent, or Firm*—Schwegman, Lunderberg, Woessner & Kluth, P.A.

[57] ABSTRACT

Immortalized normal human fetal osteoblastic cells that express a temperature sensitive mutant of simian virus 40 large T antigen are provided.

15 Claims, 13 Drawing Sheets

OTHER PUBLICATIONS

A. Weisz et al., "Estrogen Induces Expression of c-fos and c-myc Protooncogenes in Rat Uterus", *Mol. Endocrinol.*, 2, 816–824 (Sep. 1988).

A. Weisz et al., "Identification of an estrogen response element upstream of the human c-fos gene that binds the estrogen receptor and the AP-1 transcription factor", *Nucl. Acids Res.*, 18, 5097–5106 (1990).

G. Wilding et al., "Effects of Steroid Hormones and Peptide Growth Factors on Protooncogene c-fos Expression in Human Breast Cancer Cells", *Cancer Res.*, 48, 802–805 (Feb. 15, 1988).

*Current Protocols in Molecular Biology;* Eds., F.M. Ausubel et al., Eds. John Wiley & Sons: New York, NY; 1989. Enclosed is the Title page, Copyright page and Contents pages (pp. iii–x).

D. Barnes et al., "Methods for Growth of Cultured Cells in Serum–Free Medium", *Anal. Biochem.*, 102, 255–270 (1980).

S.K. Chattopadhyay et al., "Quantitative studies of integration of murine leukemia virus after exogenous infection", *Proc. Natl. Acad. Sci. USA*, 73, 4095–4099 (1976).

P. Chomczynski, "A Reagent for the Single-Step Simultaneous Isolation of RNA, DNA and Proteins from Cell and Tissue Samples", *BioTechniques*, 15, 532–536 (1993).

D.S. Colvard et al., "Microassay for Nuclear Binding of Steroid Receptors with Use of Intact Cells from Small Samples of Avian and Human Tissue", *Clin. Chem.*, 34, 363–369 (1988).

E.F. Eriksen et al., "Evidence of Estrogen Receptors in Normal Human Osteoblast–Like Cells", *Science*, 241, 84–86 (Jul. 1, 1988).

M. Ernst et al., "Estradiol Effects on Proliferation, Messenger Ribonucleic Acid for Collagen and Insulin–like Growth Factor–I, and Parathyroid Hormone–Stimulated Adenylate Cyclase Activity in Osteoblastic Cells from Calvariae and Long Bones", *Endocrinology*, 125, 825–833 (1989).

M.C. Etienne et al., "Steroid Receptors in Human Osteoblast–like Cells", *Eur. J. Cancer*, 26, 807–810 (1990).

W. Fiers et al., "Complete nucleotide sequence of SV40 DNA", *Nature*, 273, 113–120 (May 11, 1978).

T.K. Gray et al., "17β–Estradiol acts directly on the clonal osteoblastic cell line UMR106", *Proc. Natl. Acad. Sci.*, 84, 6267–6274 (1987).

T.C. Spelsberg, "Bone Cell Proto–Oncogene Promoters", National Institute of Health Grant No. AR41652.

T.C. Spelsberg, "Sex Steroids, Growth Factors and Bone Cell Function", National Institute of Health Grant No. AG04875.

M. Bodo et al., "Effects of Steroids on Human Normal and Otosclerotic Osteoblastic Cells: Influence on thymidine and Leucine Uptake and Incorporation," *Cell. Mol. Biol.*, 37, 597–606 (1991).

E. Canalis et al., "Insulin–like growth factor I mediates selective anabolic effects of parathyroid hormone in bone cultures," *J. Clin. Invest.*, 83, 60–65 (Jan. 1989).

S.A. Harris et al., "Development and Characterization of a Conditionally Immortalized Human Fetal Osteoblastic Cell Line," *J. of Bone and Min. Res.*, 10, 178 (1995).

T. Katagiri et al., "The non–osteogenic mouse pluripotent cell line, C3H10T1/2, is induced to differentiate into osteoblastic cells by recombinant human bone morphogenetic protein-2," *Biochem. Biophys. Res. Comm.*, 172, 295–299 (Oct. 15, 1990).

T. Katagiri et al., "Bone morphogenetic protein–2 converts the differentiation pathway of C2C12 myoblasts into the osteoblast lineage," *J. Cell Biol.*, 127, 1755–1766 (Dec., 1994).

C. Liu et al., "Human parathyroid hormone–(1–34) prevents bone loss and augments bone formation in sexually mature overiectomized rats," *J. Bone Miner. Res.*, 5, 973–982 (1990).

C. Marcelli et al., "In vivo effects of human recombinant transforming growth factor beta on bone turnover in normal mice," *J. Bone Miner. Res.*, 5, 1087–1096 (1990).

T.M. Murray et al., "Human parathyroid hormone carboxy-terminal peptide (53–84) stimulates alkaline phosphatase activity in dexamethasone–treated rat osteosarcoma cells in vitro," *Endocrinology*, 124, 1097–1099 (Feb., 1989).

M. Noda et al., "In vivo stimulation of bone formation by transforming growth factor–β," *Endocrinology*, 124, 2991–2994 (May, 1989).

J. Price et al., "The Cell Biology of Bone Growth," *Eur. J. Clin. Nutr.*, 48, Suppl. 1, S131–49 (Feb. 1994).

L. Quarles, "Paradoxical Toxic and Trophic Osseous Actions of Aluminum: Potential Explanations," *Miner. Electrolyte Metab.*, 17, 233–239 (1991).

J. Reeve et al., "Anabolic effects of human parathyroid hormone fragment on trabecular bone in involutional osteoporosis: a multicentre trial," *Brit. Med. J.*, 280, 1340–1344 (Jun. 7, 1980).

P.G. Robey et al., "Osteoblasts synthesize and respond to transforming growth factor–type beta (TGF–β) in vitro," *J. Cell Biol.*, 105, 457–463 (Jul., 1987).

D.M. Slovik et al., "Short–term effects of synthetic human parathyroid hormone–(1–34) administration on bone mineral metabolism in osteoporotic patients," *J. Clin. Invest.*, 68, 1261–1271 (Nov., 1981).

R.S. Thies et al., "Recombinant human bone morphogenetic protein–2 induces osteoblastic differentiation in W–20–17 stromal cells," *Endocrinology*, 130, 1318 (Mar., 1992).

E.A. Wang et al., "Recombinant human bone morphogenetic protein induces bone formation," *Proc. Natl. Acad. Sci. USA*, 87, 2220–2224 (Mar., 1990).

J.M. Wozney et al., "Novel regulators of bone formation: Molecular clones and activities," *Science*, 242, 1528–1534 (1988).

A. Yamaguchi et al., "Recombinant human bone morphogenetic protein–2 stimulates osteoblastic maturation and inhibits myogenic differentiation in vitro," *J. Cell Biol.*, 113, 681–687 (May, 1991).

Y. Aoi et al., "Newly Synthesized Glycoproteins in Plasma Membranes of Cells Transformed by SV40 and Its Gene A Function", *Tohoku J. exp. Med.*, 131, 95–96 (1980).

M.A. Aronow et al., "Factors That Promote Progressive Development of the Osteoblast Phenotype in Cultured Fetal Rat Calvada Cells", *J. Cell. Physiol.*, 143, 213–221 (1990).

M.M. Bradford, "A Rapid and Sensitive Method for the Quantitation of Microgram Quantites of Protein Utilizing the Principle of Protein–Dye Binding", *Anal. Biochem.*, 72, 248–254 (1976).

J.S. Butel et al., "Transformation of Primate and rodent Cells by Temperature–sensitive Mutants of ISV40", *Tumor Viruses*, 39, 25–36 (1975).

H. Chiba et al., "Establishment and Characterization of a Simian Virus 40–Immortalized Osteoblastic Cell Line from Normal Human Bone", *Jpn. J. Cancer Res.*, 84, 290–297 (Mar. 1993).

C.L. Chen et al., "Characterization of endocrine cell lines immortalized by a temperature–sensitive mutant SV40", *Chinese Journal of Physiology*, 34, 65–80 (1991) (Abstract only).

J.Y. Chou, "Differentiated Mammalian Cell Lines Immortalized by Temperature–Sensitive Tumor Viruses", *Mol. Endocrinol.*, 3, 1511–1514 (1989).

J.A. DeCaprio et al., "SV40 Large Tumor Antigen Forms a Specific Complex with the Product of the Retinoblastoma Susceptibility Gene", *Cell*, 54, 275–283 (Jul. 15, 1988).

L.W. Fisher et al., "Purification and Partial Characterization of Small Proteoglycans I and II, Bone Sialoproteins I and II, and Osteonectin from the Mineral Compartment of Developing Human Bone", *J. Bio. Chem.*, 262, 9702–9708 (1987).

R.T. Franceschi et al., "1α,25-Dihydroxyvitamin $D_3$ Specific Regulation of Growth, Morphology, and Fibronectin in a Human Osteosarcoma Cell Line", *J. Cell. Physiol.*, 123, 401–409 (1985).

L. Fransen et al., "Changes in Gene Expression and Protein Phosphorylation in Murine Cells, Transformed or Abortively Infected with Wile Type and Mutant Simian Virus 40", *J. Biol. Chem.*, 258, 5276–5290 (1983).

C.-H. Heldin et al., "A human osteosarcoma cell line secretes a growth factor structurally related to a homodimer of PDGF A-chains", *Nature*, 319, 511–514 (1986).

G. Helftenbein et al., "Establishment of a temperature–dependent cell line from rat endometrium by retroviral infection", *Eur. J. Cell Biol.*, 56, 49–57 (1991).

J. Imbert et al., "Stabilization of the Large T Protein in Temperature–Independent (Type A) FR 3T3 Rat Cells Transformed with the Simian Virus 40 tsA30 Mutant", *J. Virol.*, 47, 442–451 (1983).

H.C. Isom et al., "Transformation of Isolated Rat Hepatocytes with Simian Virus 40", *J. Cell Biol.*, 85, 651–659 (1980).

P.E. Keeting et al., "Development and Characterization of a Rapidly Proliferating, Well–Differentiated Cell Line from Normal Adult Human Osteoblast–like Cells Transfected with SV40 Large T Antigen", *J. Bone Min. Res.*, 7, 127–136 (1992).

M. Kirstein et al., "Tumor Necrosis Factor Stimulates Proliferation of Human Osteosarcoma Cells and Accumulation of c–myc Messenger RNA", *J. Cell. Physiol.*, 134, 479–484 (1988).

J. Koniecki et al., "Effect of the SV40 T Antigen on the Posttranscriptional Regulation of the Proliferating Cell Nuclear Antigen and DNA Polymerase–α Genes", *Cancer Research*, 51, 1465–1471 (1991).

C. Lafarge–Frayssinet et al., "Expression of Gamma–Glutamyl Transpeptidease in Adult Rat Liver Cells After Transformation with SV40 Virus", *Cancer Letters*, 22, 31–39 (1984).

R. Langer et al., "Tissue Engineering", *Science*, 260, 920–926 (May 14, 1993).

J.W. Ludlow et al., "SV40 Large T Antigen Binds Preferentially to an Underphosphorylated Member of the Retinoblastoma Susceptibility Gene Product Family", *Cell*, 56, 57–65 (Jan. 13, 1989).

T.J. Martin et al. "Hormonal Influence on Bone Cells", *Methods Enzymol.*, 145, 324–336 (1987).

T. Matsumura et al., "Studies of SV40–Infected Werner Syndrome Fibroblasts", *Adv. Exp. Med. Biol.*, 190, 313–330 (1985).

T. Mitsudomi et al., "Abortive Transformation of Temperature–Sensitive Mutants of Rat 3Y1 Cells by Simian Virus 40: Effect of Cellular Arrest States on Into S Phase and Cellular Proliferation", *J. Cell. Physiol.*, 123, 353–360 (1985).

D.S. Neufled et al., "Immortalization of Human Fibroblasts Transformed by Origin–Defective Simian Virus 40", *Mol. Cell Biol.*, 7, 2794.2802 (Aug. 1987).

C.A. Noonan et al., "Characterization of Simian Cells Transformed by Temperature–Sensitive Mutants of Simian Virus 40", *J. Virol.*, 18, 1106–1119 (1976).

K. Onodera et al., "Alterations in surface glycoproteins and level of sialyltransferase of cells transformed by a temperature–sensitive mutant of simian virus 40", *Proc. Natl. Acad. Sci. USA*, 73, 4090–4094 (1976).

T.A. Owen et al., "Coordinate occupancy of AP–1 sites in the vitamin D–responsive and CCAAT box elements by Fos–Jun in the osteocalcin gene: Model for phenotype suppression of transcription", *Proc. Natl. Acad. Sci. USA*, 87, 9990–9994 (1990).

W.A. Peck et al., "Evidence for Preferential Effects of Parathyroid Hormone, Calcitonin and Adenosine on Bone and Periosteum", *Endocrinology*, 100, 1357–1364 (1977).

V.B. Reddy et al., "The Genome of Simian Virus 40", *Science*, 200, 494–502 (May 5, 1978).

A.J. Ridley et al., "ras–mediated cell cycle arrest is altered by nuclear oncogenes to induce Schwann cell transformation", *EMBO J.*, 7, 1635–1645 (1988).

C.A. Reinhart et al., "Alterations of DNA content in human endometrial stromal cells transfected with a temperature–sensitive SV40: tetraploidization and physiological consequences", *Carcinogenesis*, 13, 63–68 (1992).

P.G. Robey et al., "Human Bone Cells In Vitro", *Calcif. Tissue Int.*, 37, 453–460 (1985).

G.A. Rodan et al., "Expression of the Osteoblastic Phenotype" in *Bone and Mineral Research*; W.A. Peck, Ed.; Elsevier, Amsterdam; 1984; pp. 244–285.

G.A. Rodan et al., "Gene Expression in Osteoblastic Cells", *Crit. Rev. Eukaryot. Gene Expr.*, 1, 85–98 (1991).

S.B. Rodan et al., "Characterization of a Human Osteosarcoma Cell Line (Saos–2) with Osteoblastic Properties", *Cancer Research*, 47, 4961–4966 (Sep. 15, 1987).

H. Rothschild et al., "Isolation and Characterization of a Heat–Inducible Simian Virus 40 Mutant", *J. Virol.*, 19, 374–381 (1976).

R.K. Schenk et al., "Preparation of calcified tissues for light microscopy" in *Methods of Calcified Tissue Preparation*; G.R. Dickson, Ed.; Elsevier, ; 1984; pp. 1–56.

P.J. Southern et al., "Transformation of Mammalian Cells to Antibiotic Resistance with a Bacterial Gene Under Control of the SV40 Early Region Promoter", *J. Mol. Appl. Gen.*, 1,327–341 (1982).

J.L Spurbeck et al., "Culturing and Robotic Harvesting of Bone Marrow, Lymph Nodes, Peripheral Blood Fibroblasts, and Solid Tumors with In Situ Techniques", *Cancer Genet. Cytogenet.*, 32, 59–66 (1988).

G.S. Stein et al., "Relationship of cell growth to the regulation of tissue–specific gene expression during osteoblast differentiation", *FASEB J.*, 4, 3111–3123 (Oct. 1990).

P. Tegtmeyer et al., "Function of Simian Virus 40 Gene A in Transforming Infection", *J. Virol.*, 15, 613–618 (Mar. 1975).

D. Wynford–Thomas et al., "Conditional Immortalization of Human Thyroid Epithelial Cells: A tool for Analysis of Oncogene Action", *Mol. Cell Biol.*, 10, 5365–5377 (Oct. 1990).

S.H. Zuckerman et al., "Transformation–Associated Changes in Nuclear–Coded Mitochondrial Proteins in 3T3 Cells and SV40–Transformed 3T3 Cells", *Bioch. Biophys. Acta.*, 804, 285–290 (1984).

U.S. Barzel, "Estrogens in the Prevention and Treatment of Postmenopausal Osteoporosis: A Review", *Am. J. Med.*, 85, 847–850 (Dec. 1988).

A. Marusic et al., "Production of Leukemia inhibitory factor mRNA and protein by malignant and immortalized bone cells", *Chem. Abs.*, 121, Abstract No. 154804 (Sep. 24, 1994).

S. Migliaccio et al., "Estrogens Modulate the Responsiveness of Osteoblast–Like Cells (ROS 17/2.8) Stably Transfected with Estrogen Receptor", *Endocrinology*, 130, 2618–2624 (1992).

C.K.W. Watts et al., "Stable Transfection of the Oestrogen Receptor Gene into a Human Osteosarcoma Cell Line", *J. Steroid Biochem.*, 34, 483–490 (1989).

Evans et al., *Bone and Mineral*, vol. 26, 1994, pp. 95–107.

Pivirotto et al., *Mol. Cell. Endocrinol.*, vol. 111, 1995, pp. 67–74.

Tsuchiya et al., *J. Orthopaedic Res.*, vol. 11, 1993, pp. 122–130.

Van der Pluijm et al., *J. Bone Min. Res.*, vol. 7, 1992, pp. 981–986.

IMMORTALIZED HUMAN FETAL OSTEOBLASTIC CELLS

The present invention was made with Government support under Grant Nos. AR41652 and AG04875 awarded by the National Institute of Health. The Government has certain rights in the invention.

BACKGROUND OF THE INVENTION

Osteoblasts are cells that arise from connective tissue precursor cells in bone marrow, and are associated with bone growth as they mature. Osteoclasts are cells associated with the absorption and removal of bone. In normal bone, the balance between osteoblast-mediated bone formation and osteoclast-mediated bone resorption is maintained through complex cell to cell interactions. Postmenopausal osteoporosis is a condition that affects millions of women and results in debilitating bone and spinal injuries. This condition is characterized by dramatic bone deterioration due to an imbalance between bone formation (by osteoblasts) and bone resorption (by osteoclasts). To determine the causes for bone deterioration associated with osteoporosis, and to devise effective treatments for this condition, the processes of osteoblast differentiation, osteoblast physiology, osteoblast-osteoclast communication, and osteoclast function must be studied further.

To gain further insight into the process of bone formation, a number of model systems utilizing osteoblastic cells in culture have been developed. The most widely used cultured osteoblastic cells include primary cultures, i.e., cell cultures made by direct transfer from a natural source to an artificial medium. These cell cultures can be derived from normal human and rodent bone tissue, as well as from osteosarcoma cells obtained from adult human and rodent tumors. See, for example, P. G. Robey et al., *Calcif. Tissue Int.*, 37, 453 (1985); W. A. Peck et al., *Endocrinology*, 100, 1357 (1977); R. T. Franceschi et al., *J. Cell Physiol.*, 123, 401 (1985); C. H. Heldin et al., *Nature*, 319, 511 (1986); S. B. Rodan et al., *Cancer Res.*, 47, 4961 (1987); M. Kirstein et al., *J. Cell Physiol.*, 134, 479 (1988); G. A. Rodan et al. In *Bone and Mineral Research*, W. A. Peck, eds. (Elsevier), 244 (1984); and T. J. Martin et al., *Methods Enzymol.*, 145, 324 (1987). These model systems, as well as other osteoblastic cell systems, have contributed greatly to the understanding of osteoblast biology. However, each of these model systems have limitations with regard to their application to the study of human osteoblast biology and hormones or growth factors. Furthermore, they cannot be used in methods of treating a human for bone loss.

Osteoblastic cultures derived from rodent species may exhibit species-specific phenotypic characteristics which differ from those of human osteoblastic cultures. Osteosarcoma cells have a different phenotype than untransformed cells, and an unknown genetic transforming event (G. A. Rodan et al., *Crit. Rev. Eukaryot. Gene Expr.*, 1, 85 (1991)). Thus, they may respond abnormally to hormone or growth factor treatment. Primary cultures derived from normal adult human bone, have an osteoblastic phenotype but proliferate at a very slow rate and become senescent after a relatively short time in culture. Thus, as a result of the slow growth and limited life span in culture, these cells are of limited utility.

To avert the limitations attributed to these cell systems, a HOBIT (human osteoblast-like initial transfectant) cell line was developed. These cells were derived from primary cultures of adult human bone cells transfected with a gene expressing the SV40 large T antigen (P. E. Keeting et al., *J. Bone Min. Res.*, 7, 127 (1992)). Similarly, other laboratories have reported the establishment of human bone cell primary cultures infected with SV40 virus (H. Chiba et al., *Jpn. J. Cancer Res.*, 84, 290 (1993)). Although these latter cells were developed from normal fetal bone cells, they are not homogeneous populations. While these adult and fetal SV40-transformed cells express many osteoblast phenotypic markers, the expression of the SV40 large T antigen (T Ag) is constitutive, and thus cannot be manipulated. Further, the utility of osteoblastic cells infected with wild type SV40 virus is limited by other considerations, such as nonclonal derivation and the expression of other viral proteins. As a result, variations in phenotype within cell subpopulations may exist, or phenotypic changes induced by viral infection may occur.

Thus, what is needed are osteoblastic cells derived from normal human cells that overcome these disadvantages. Specifically, what is needed are osteoblastic cells that could be cultured indefinitely, proliferate rapidly, and be propagated continually using routine cell culture techniques.

SUMMARY OF THE INVENTION

The present invention provides immortalized normal human fetal osteoblastic (hFOB) cells. As used herein, "immortal" or "immortalized" cells refer to a substantially continuous and permanently established line of cells with substantially unlimited cell division potential. That is, the cells can be cultured substantially indefinitely, i.e., for at least about 6 months under rapid conditions of growth, preferably much longer under slower growth conditions, and can be propagated rapidly and continually using routine cell culture techniques. Alternatively stated, the cells of the present invention can be cultured for at least about 100 population doublings. These cells produce a complement of proteins characteristic of normal human osteoblastic cells and are capable of osteoblastic differentiation. They can be used in cell culture studies of osteoblastic cell sensitivity to various agents, such as hormones, cytokines, and growth factors, or in tissue therapy.

Specifically, the present invention provides immortalized human fetal osteoblastic cells which express a temperature sensitive mutant of simian virus 40 (SV40) large T protein antigen (TAs). These cells are part of an established cell line; however, they are generally nontumorogenic, i.e., they do not form tumors in mammals. They are preferably part of a homogeneous population. Preferably, the homogeneous population is a clonal population. As used herein, "clonal" cells refer to a homogeneous population of cells derived from a single progenitor cell.

In one embodiment of the invention, human fetal bone cells, isolated from human fetal tissue, are transfected with a gene coding for a temperature-sensitive (ts) mutant of SV40 large T antigen to yield immortalized human fetal osteoblastic cells, designated herein as hFOB 1.19. As used herein, "transfection" refers to a process by which foreign DNA is introduced into eucaryotic cells and translocated from the cytoplasm to the nucleus, where it is incorporated into the genome and expressed. The DNA is typically included in an expression vector, such as a circular or linearized plasmid vector. In the preparation of a preferred embodiment of the present invention, human fetal bone cells are transfected by electroporation with the expression vector pUCSVtsA58. Additionally, the human fetal tissue cells can be transfected with a selectable marker gene, such as a gene coding for resistance to an agent normally toxic to the untransformed cells, such as an antibiotic, an antineoplastic agent, or a herbicide. In the preparation of another preferred embodiment of the present invention, human fetal bone cells transfected with a gene for ts mutant of SV40 T Ag are also transfected with the expression vector pSV2neo.

Although the cells of the present invention are prepared by transfecting with the gene coding for a temperature-sensitive mutant of the SV40 large T antigen that is incorporated into the expression vector pUCSVtsA58, gene fragments or mutations of this gene can be used as long as they impart temperature regulation to the resultant immortalized cells as defined herein. Furthermore, other genes, gene fragments, or mutations coding for a temperature-sensitive mutant of the SV40 large T antigen that impart temperature regulation to the resultant cells can be used.

Although the cells of the present invention are referred to as immortalized, they could alternatively be referred to as transfected or transformed. Advantageously, they are normal cells that are conditionally immortalized. By this it is meant that the large T antigen is capable of being inactivated. Although the cells are still viable and express proteins, they can be put into a state of low proliferation. That is, preferred immortalized human fetal osteoblastic cells of the present invention can undergo rapid cell division, or little or no cell division as a result of inactivating the large T antigen. This inactivation can occur by increasing the temperature of incubation of the cell cultures. For example, at a temperature at or less than about 37° C., preferably about 33°–36° C., rapid cell division occurs, whereas at a temperature above about 37° C. little or no cell division occurs. Rather differentiation occurs at elevated temperatures. Preferably and advantageously, the cells of the present invention can be cycled between an active and an inactive state, i.e., the large T antigen can be cyclicly activated and inactivated. In this way, cells of different phenotypes can be propagated from the immortalized normal human fetal cells of the present invention.

The preferred cells of the present invention have the identifying characteristics of ATCC CRL 11372. That is, they are clonal, conditionally immortalized normal human fetal cells capable of osteoblastic differentiation. They differ from transformed osteosarcoma cells in that they have the ability to differentiate into mature osteoblasts expressing the normal osteoblast phenotype. Thus, the cells of the present invention provide a homogenous, rapidly proliferating model system for studying normal human osteoblast differentiation, osteoblast physiology, and hormonal, growth factor, and other cytokine effects on osteoblast function and osteoblast differentiation.

Accordingly, another aspect of the present invention provides a method of testing a drug, i.e., a biological or chemical agent, for effects on osteoblastic cell physiology. This method involves exposing a culture of immortalized normal human fetal osteoblastic cells which express a temperature sensitive mutant of simian virus 40 large T antigen to the drug and monitoring at least one of the resultant changes in the physiology of the cultured cells. These cellular changes can be any of a variety of changes of interest. This includes, for example, monitoring secretion of growth factors and other cytokines, growth of osteoblastic cells, expression of osteoblast associated genes, formation of mineralized nodules, mineralization of an extracellular matrix, or formation of bone. If the drug under investigation is added to a culture of cells of the present invention at various incubation temperatures, its effect on different osteoblastic phenotypes can be investigated. For example, if the cells are incubated at a restrictive temperature, i.e., greater than about 37° C., preferably greater than about 38° C., and more preferably greater than about 39° C., cell division is slowed, differentiation increases, and a more mature osteoblast phenotype is produced. Thus, preferred embodiments of the present invention include adding a drug for evaluation to a culture of immortalized human fetal undifferentiated osteoblastic cells wherein the cells are cultured at a temperature no greater than about 37° C. Alternatively, a drug can be added to a culture of cells wherein the cells are cultured at a temperature greater than about 37° C. for evaluation of the drug's effect on a different phenotype, e.g., more mature phenotype, of the cells.

Furthermore, the present invention is directed to a method of treating bone loss in a mammal, e.g., a human. This method involves placing immortalized human fetal osteoblastic cells which express a temperature sensitive mutant of simian virus 40 large T antigen into or onto a deteriorated bone at the point of deterioration. As used herein, "deteriorated bone" refers to one that has deteriorated as a result of osteoporosis, bone fracture, bone break, or bone loss around a surgical implant. The cells are placed into the bone at the point of deterioration, fracture, or break in an amount effective to cause or induce new bone formation/replacement.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
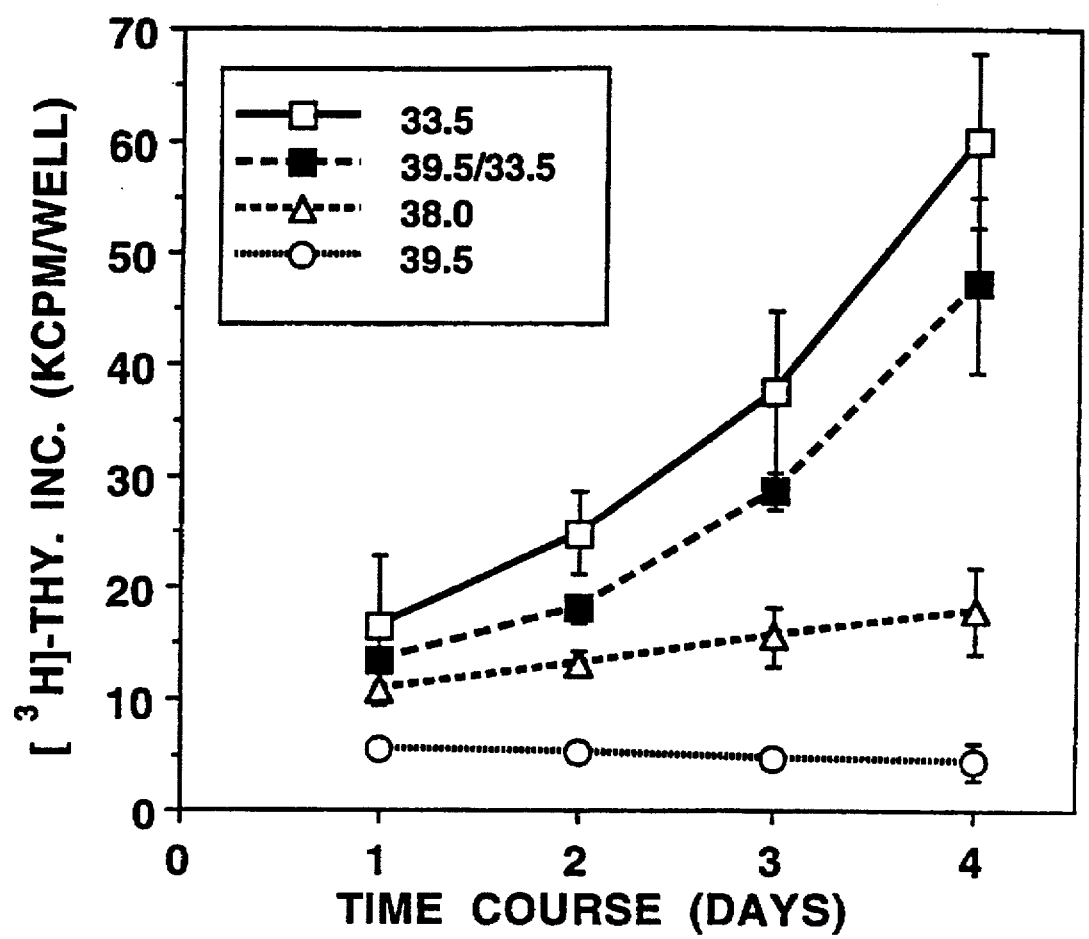
FIG. 1. Thymidine incorporation of hFOB 1.19 cells cultured at various temperatures. Subconfluent hFOB cultures were cultured at the indicated temperatures for 24 hrs, then pulsed with $^3$H-labeled thymidine for 24 hrs for each day of the time course. Except that 39.5/33.5 indicates that the cells were cultured at 39.5° C. for 24 hrs, then returned to 33.5° C. for the remainder of the time course. Thymidine incorporation was measured after each pulse labelling. Error bars=1 standard deviation, n=4.
Figure 2A:
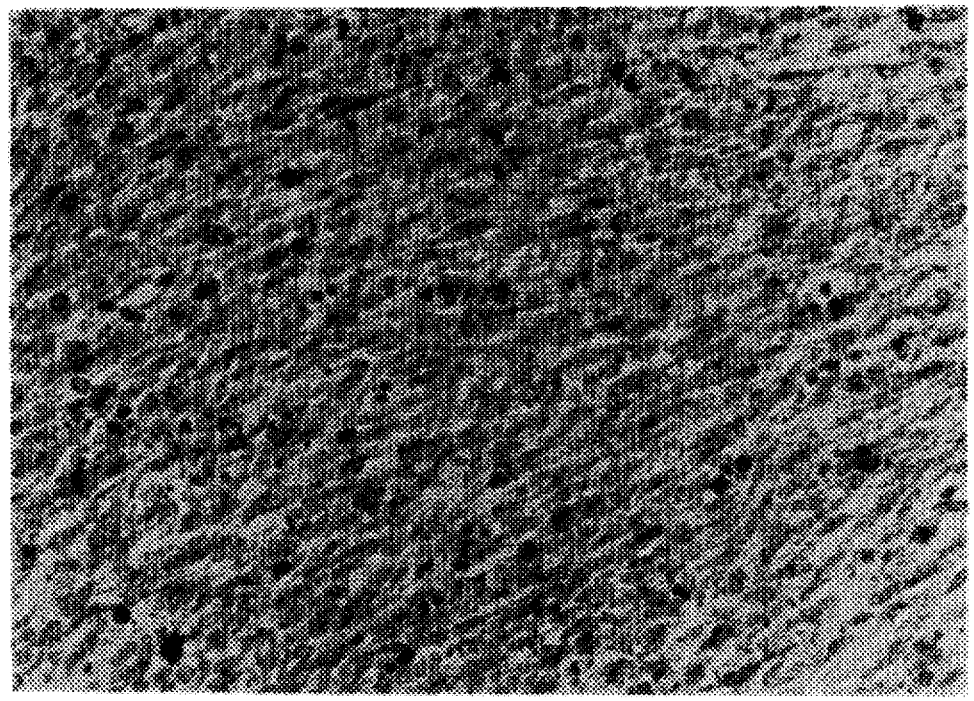
FIG. 2. Immunostaining of postconfluent hFOB 1.19 cells for osteoblast phenotypic markers. Postconfluent (day 8 after confluence) hFOB 1.19 cells cultured at 33.5° C. were stained by an immunoperoxidase method using primary antibodies (Ab) specific to: (A) OP; (B) ON; (C) OC; (D) BSP; (E) type I collagen; (F) no primary Ab; (G) SV40 T Ag; and (H) no primary Ab for T Ag. Dark (i.e., red) staining indicates areas where each protein (bound by Ab) is localized (100× magnification).
Figure 2B:
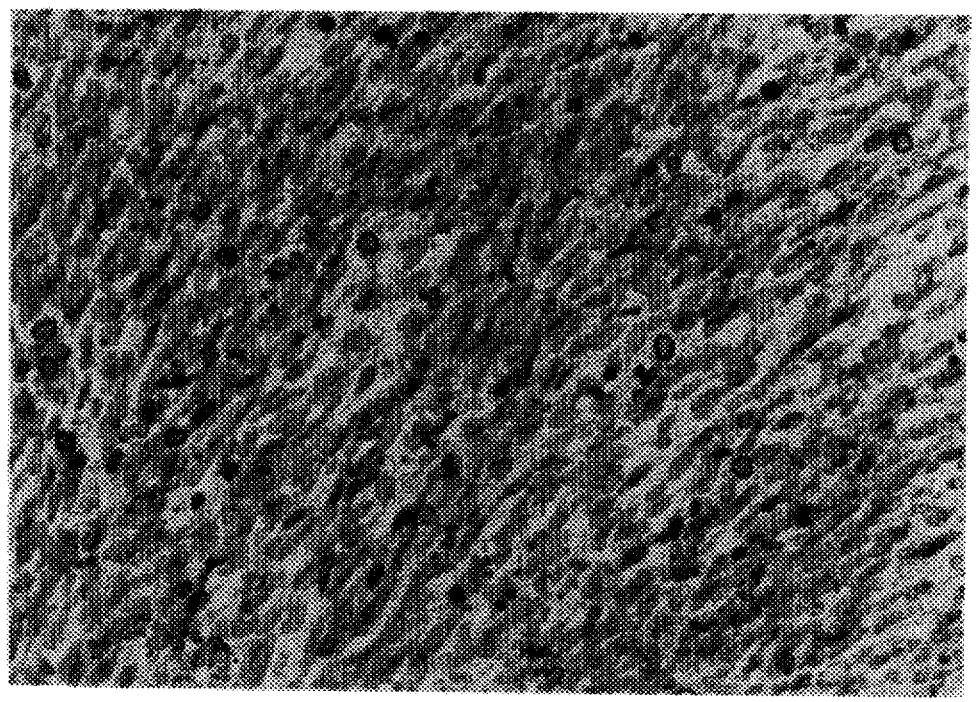
Figure 2C:
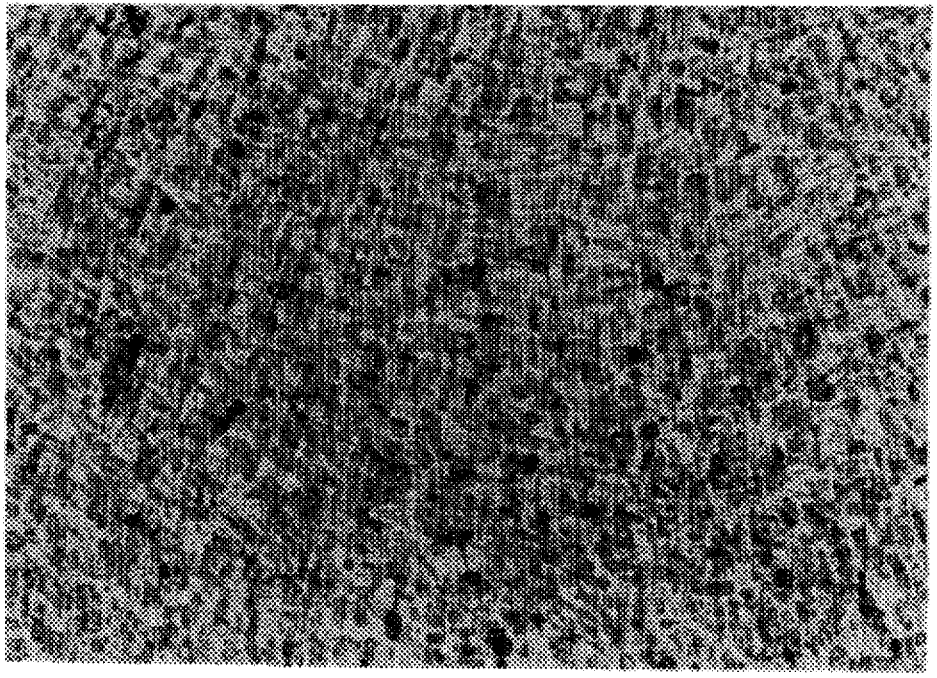
Figure 2D:
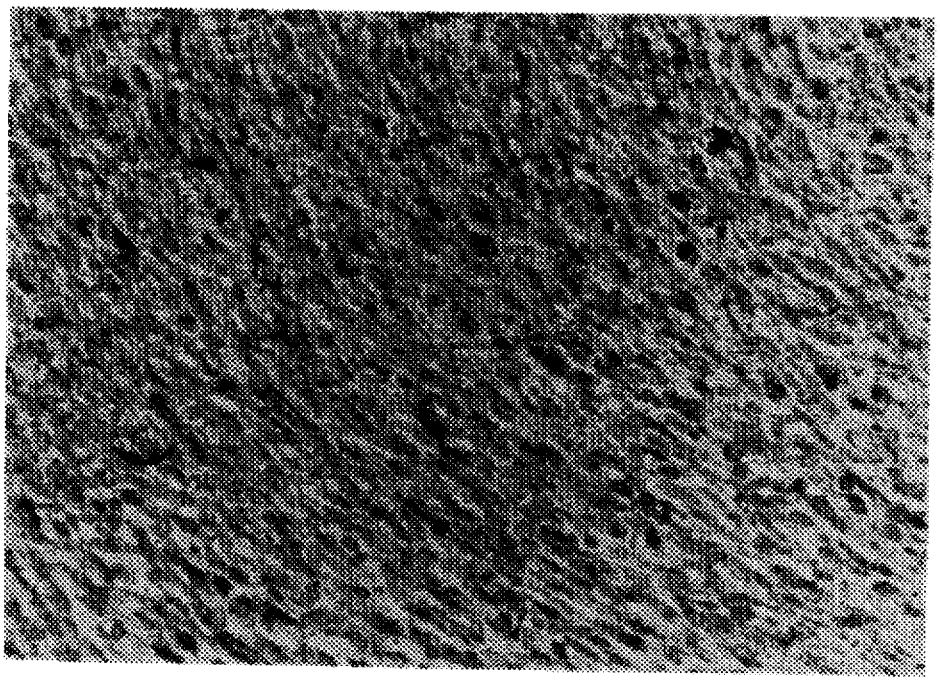
Figure 2E:
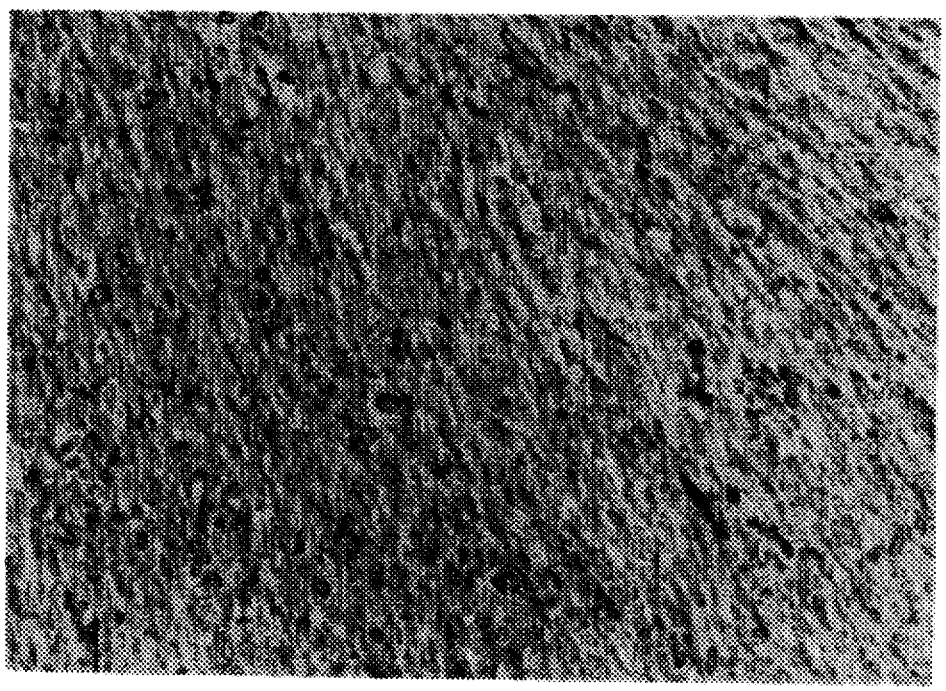
Figure 2F:
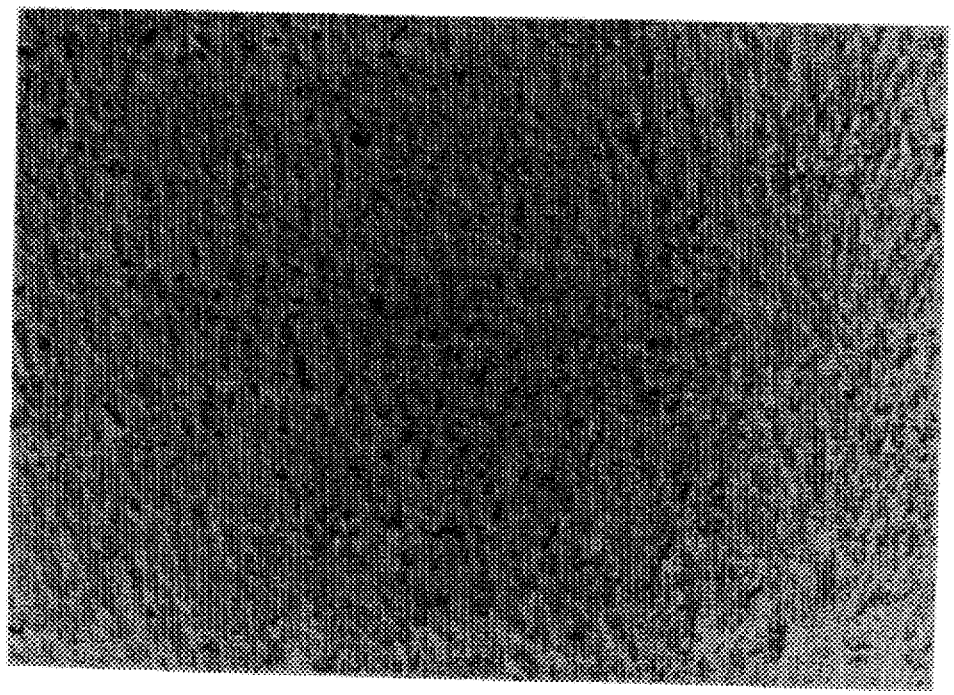
Figure 2G:
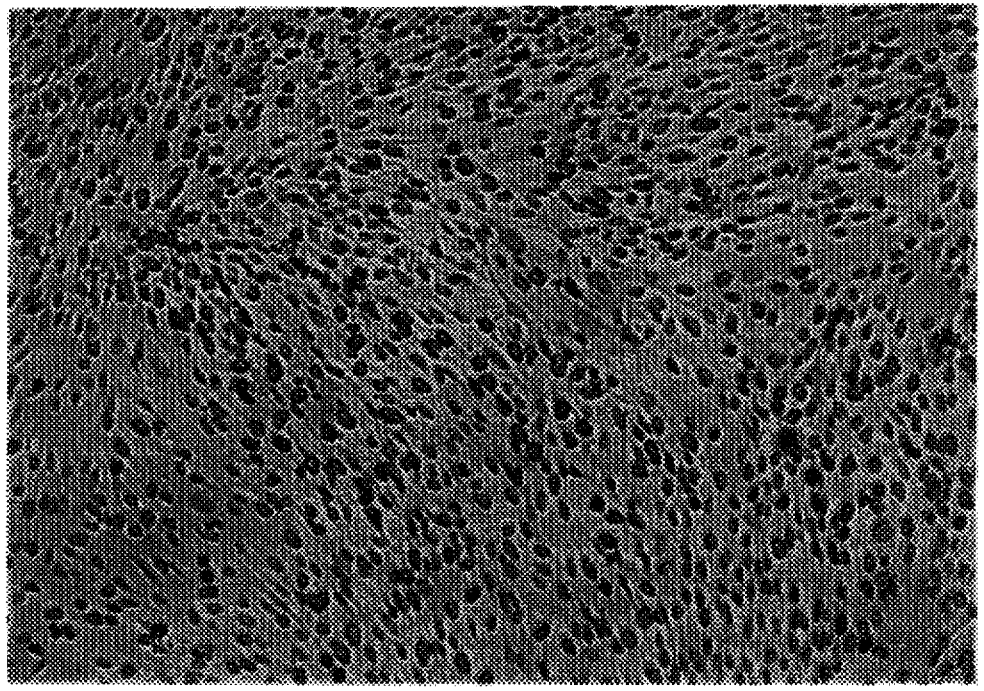
Figure 2H:
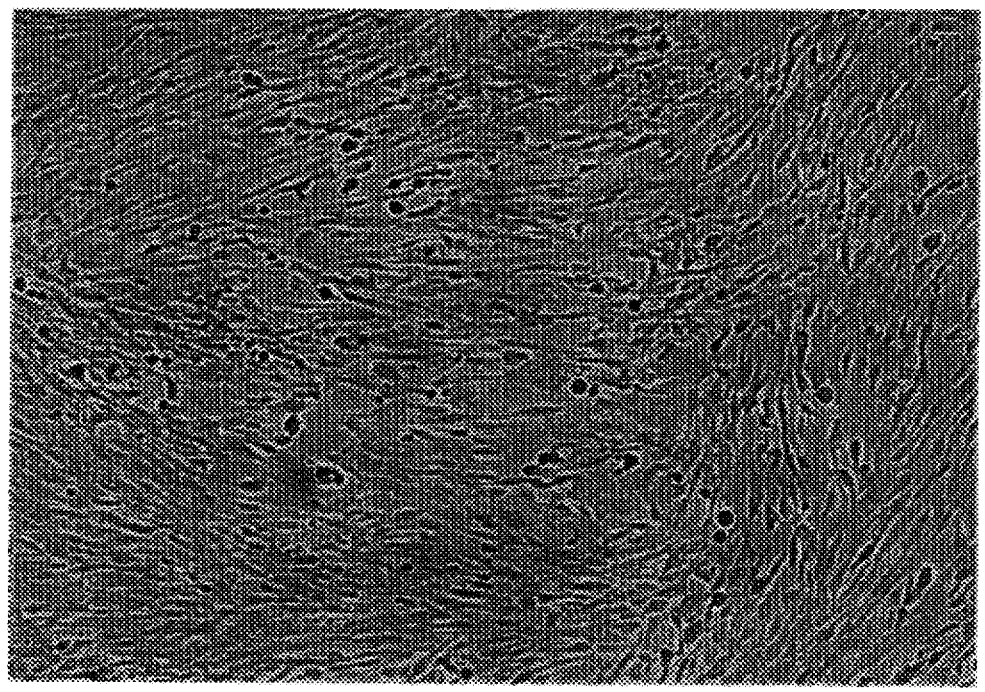

The present invention is directed to human normal fetal osteoblastic cells that are conditionally immortalized with a gene coding for a temperature-sensitive (ts) mutant (tsA58) of SV40 large T antigen (T Ag). This gene product termed early gene or large T antigen is responsible for immortalizing cells; however, the mechanism by which this occurs is unknown. The expression vector alone has no effect. Expression of T Ag in human cells results in an increased and prolonged rate of proliferation, which is believed to result from interaction of T Ag with the retinoblastoma gene product, Rb. Under conditional immortalization, however, the mutant T Ag is only active (immortalized) at a temperature referred to herein as "permissive" temperature. Thus, the return to an inactive (nonimmortalized) state can be manipulated by changing the incubation of the cells to a restrictive (nonpermissive) temperature. This type of conditional immortalization has been used successfully in other cell types. See, for example, J. Y. Chou, *Mol. Endocrinol.*, 3, 1511 (1989).

Thymidine incorporation experiments indicate that expression of this gene at the permissive temperature, which is at or less than about 37° C., preferably about 33°–36° C., and more preferably at a temperature of about 33.5° C., results in rapid cell proliferation. When hFOB cells are cultured at an elevated temperature, i.e., at a temperature greater than about 37° C., preferably at about 38° C., cell proliferation slows considerably. Typically, proliferation does not occur at a restrictive temperature of 39.5° C. These results suggest that the conditional immortalization is dependant on a functional large T antigen The resumption of rapid cell proliferation following conversion from the restrictive to the permissive temperatures is consistent with this hypothesis.

The differentiation of osteoblastic cells in culture involves a programmed developmental sequence. This sequence is characterized by an early proliferative stage during which osteoblastic cells are relatively undifferentiated, and later postconfluent stages which involve the expression of bone cell phenotypic markers and ultimately extracellular matrix mineralization. See, for example, M. A. Aronow et al., *J. Cell Physiol.*, 143, 213 (1989); and G. S. Stein et al., *FASEB J.*, 4, 3111 (1990).

There are numerous phenotypic markers and characteristics associated with osteoblast differentiation. These include: the expression of alkaline phosphatase (AP), osteopontin (OP), osteonectin (ON), osteocalcin (OC), bone sialoprotein (BSP), and type I collagen; an increase in cellular cAMP levels in response to parathyroid hormone (PTH); an increase in OC levels in response to 1,25-$(OH)_2D_3$ treatment; and the formation of a mineralized matrix. hFOB cells express high levels of all of the above-mentioned osteoblast-associated proteins in postconfluent cultures. The expression of these phenotypic markers is indicative of stages of osteoblast differentiation which follow confluency in culture. Further, OC levels increase in response to 1,25-(OH)$_2D_3$ treatment, and cAMP levels increase in response to PTH treatment in postconfluent hFOB cells. These data suggest that hFOB cells contain functional vitamin D receptors and PTH receptors. In addition, hFOB cells form mineralized nodules in postconfluent cultures, which is characteristic of the late stages of osteoblast differentiation in culture. Therefore, hFOB cells appear to be relatively undifferentiated cells programmed to differentiate upon reaching confluence into cells which possess the full spectrum of osteoblast-associated features.

The conditional nature under which hFOB cells are immortalized prompted further investigation into the effect of cell proliferation on the expression of genes associated with osteoblast differentiation. Both alkaline phosphatase and 1,25-$(OH)_2D_3$-induced osteocalcin expression in postconfluent hFOB cells are significantly affected by incubation temperature. Since the incubation of hFOB cells at a restrictive temperature of about 39.5° C. results in the inactivation of the temperature sensitive SV40 T Ag and a subsequent decrease in cell proliferation, the affect on AP and OC gene expression suggests that changes in T antigen activity and subsequent effects on cell proliferation affect cell differentiation. It is possible that AP and OC expression are regulated by nuclear factors such as FOS and JUN, which are associated with cell proliferation. However, it is also possible that retinoblastoma may directly effect OC and AP gene expression, since the inactivation of SV40 large T Ag would affect Rb activity. However, the invention is not limited by any particular mechanistic theory of action.

As stated above, the cells of the present invention can be used in cell culture studies of osteoblastic cell sensitivity to various agents, such as hormones, cytokines, and growth factors, or in tissue therapy. For example, they can be used in testing drugs by adding a drug to a culture of cells of the present invention at various incubation temperatures. In this way the drug's effect on different osteoblastic phenotypes can be investigated. Furthermore, the cells of the present invention can be used in a method of treating bone loss, e.g., resulting from osteoporosis, a fracture or break, and/or bone loss around the site of a surgical implant. This method involves placing immortalized human fetal osteoblastic cells which express a temperature sensitive mutant of simian virus 40 large T antigen into or onto a deteriorated bone at the point of deterioration. Specific methods and techniques used in such a tissue therapy regime are generally described by R. Langer et al., *Science*, 260, 920 (1993), which is incorporated herein by reference.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL EXAMPLES

Materials

Delbecco's minimal essential media/Ham's F12 (DMEM/F12 1:1 w/w) mix, menadione (vitamin $K_3$), ascorbic acid (vitamin C), human parathyroid hormone fragment 1–34 (PTH 1–34), prostaglandin $E_2$ ($PGE_2$, 11,15-dihydroxy-9-oxoprosta-5,13-dien - 1 oic acid), forskolin (7β-acetoxy-1 α,6β,9α-trihydroxy-8,13-epoxy-labd-14-en-11-one), and the alkaline phosphatase enzyme assay kit were purchased from Sigma Chemical Co. (St. Louis, Mo.). Fetal Bovine Serum (FBS) was purchased from Flow Laboratories Inc. (McLean, Va.) and 1,25-dihydroxy vitamin $D_3$ (1,25-(OH)$_2D_3$) was purchased from Biomol (Plymouth Meeting, Pa.). Neomycin G418 (geneticin) was purchased from Gibco Laboratories (Gaithersburg, Md.) and electroporation cuvettes were purchased from Bio-Rad Laboratories (Hercules, Calif.). The substrate-based staining kit for alkaline phosphatase was purchased from Vector Laboratories Inc. (Burlingame, Calif.) and the human osteocalcin RIA kit was purchased from Immutopics (San Clemente, Calif.). The cAMP assay kit was purchased from Amersham Corp. (Arlington Heights, Ill.) and the peroxidase immunostaining kit was purchased from Biomeda Corp. (Foster City, Calif.). The SV40 T Ag-specific monoclonal antibody was purchased from Oncogene Science (Uniondale, N.Y.) and $^3$H-labelled thymidine was purchased from New England Nuclear Research Products, DuPont Company (Boston, Mass.). Polyclonal antibodies specific for human osteopontin (OP) LF-7, osteonectin (ON) LF-BON, osteocalcin (OC) LF-32, bone sialoprotein (BSP) LF-100, and type I collagen LF-67 were obtained from Dr. Larry W. Fisher at the Bone Research Branch, National Institute of Dental Research, National Institutes of Health, Bethesda, Md. 20892. See also, L. W. Fisher et at., *J. Biol. Chem.*, 262, 9702 (1987), which is incorporated herein by reference. The T Ag expression vector pUCSVtsA58 is available from D. Wynford-Thomas without restriction of use (Department of Pathology, CRC Thyroid Tumour Biology Research Group, University of Wales College of Medicine, Heath Park, Cardiff CF4 4XN, United Kingdom). See also D. Wynford-Thomas et al., *Mol. Cell. Biol.*, 10, 5365 (1990); P. Tegtmeyer, *J. Viorology*, 15, 613 (1975); and A. J. Ridley et al., *Embo. J.*, 7, 1635 (1988). The neomycin resistance expression vector pSV2neo was purchased from American Type Culture Collection (Rockville, Md.).

Isolation, Transfection, and Screening of hFOB Cells

Limb tissue was obtained from a spontaneous miscarriage under institutionally approved protocols as a source for primary cultures. The limb tissue was placed in phosphate buffered saline and homogenized with scalpel blades, then digested with collagenase (0.5 mg/ml) for 30 rain and trypsin (10 mg/ml) for 30 min. The cells were then seeded into 100 mm tissue culture plates containing phenol red-free DMEM/F12 media with 10% (v/v) FBS and 10% (v/v) human serum. The cells were incubated at 37° C. in 5% $CO_2$ humidified air and the media was replaced every 48 hrs until sufficient numbers of cells were present for the transfection procedure. Cells which did not adhere to the culture plates were discarded. Adherent cells were removed from the culture plates with trypsin-EDTA treatment. Briefly, cells were rinsed with phosphate buffered saline (PBS). Then a 10× stock solution of trypsin-EDTA obtained from SIGMA Chemical was diluted 10 fold with PBS and enough 1× solution was added to cover the surface of the culture plate and incubated at 37° C. until the adherent cells were released. The cells were then rinsed with serum-containing media and centrifuged (5 min at 900 ×g), then rinsed again with serum-free media and centrifuged (5 min at 900 ×g).

The pellet of cells (containing approximately 8 ×10$^6$) was resuspended in 0.4 ml of serum free media containing 10 µg of linearized T Ag expression vector pUCSVtsA58 and 2 µg of linearized neomycin resistance expression vector pSV2neo (P. J. Southern et at., *J. Mol. Appl. Gen.*, 1,327 (1982)). The cell/DNA suspension was placed in an electroporation cuvette and incubated at 4° C. for 10 min. The cells were then subjected to a pulse of 900 V/cm at 960 µFD using a Biorad electroporation device and incubated at 4° C. for 10 min more following the pulse. The cells were then seeded into tissue culture plates containing DMEM/F12 media with 10% (v/v) FBS at 37° C. After 48 hrs and every 48 hrs thereafter, the media was replaced with fresh media containing 600 µg/ml neomycin G418. After 7–10 days of neomycin selection, resistant colonies were visible and were maintained in media containing 300 µg/ml neomycin G418. More than 50 neomycin resistant colonies were passaged by trypsin-EDTA treatment in glass cylinders and seeded into separate tissue culture wells for further growth and screening.

When sufficient numbers of cells from each colony were obtained, they were screened for alkaline phosphatase activity by a substrate-based staining technique according to the manufacturer's specifications, as described in the substrate-based staining kit for alkaline phosphatase purchased from Vector Laboratories Inc. Briefly, confluent cells were rinsed twice with PBS and fixed with absolute ethanol. Then alkaline buffer (100 mM Tris-HCl pH 9.5) containing substrate was added to the cells and incubated at 37° C. for 30 min. Five of the colonies which were screened had high levels of AP activity (were heavily stained). The highest activity was observed in the clone hFOB 1.19.

Thymidine Incorporation

The hFOB cells were seeded at low density (5×10$^3$ cells/well, 48 well dish) in the DMEM/F12 media with 10% (v/v) FBS and cultured for 16–18 hours at 33.5° C. The cells were then cultured for 24 hrs at the test temperature (33.5° C., 38.0° C., 39.5° C.), and then pulsed with 0.5 µCi of $^3$H-labelled thymidine for 24 hrs for each day of the time course. After each thymidine pulse, the cells were rinsed three times with 10% (w/v) trichloroacetic acid, then solubilized in 0.2% (w/v) sodium hydroxide. The solute was then mixed with scintillation cocktail for quantitation of $^3$H in a Beckman model LS2800 scintillation counter.

Karyotype Analysis

Karyotype analysis was performed in the Mayo Cytogenetics Laboratory by the method described in J. L. Spurbeck et al., *Cancer Genet. Cytogenet.*, 32, 59 (1988), as detailed for fibroblast cultures, which is incorporated herein by reference. Briefly, hFOB cells were seeded at low density on glass coverslips in tissue culture dishes. At 10–30% confluence, the cells were treated with 0.25 µg/ml colcemid for 30–60 min. The cells were then prepared for metaphase spreads using a Tecan model 505 robotic sample processor.

Immunocytochemistry.

Immunostaining for SV40 T Ag was performed by fixing subconfluent hFOB cells with 100% methanol for 10 min at 4° C., then blocking in 1% bovine serum albumin (BSA) in PBS for 60 min. Primary antibody (in 1% BSA in PBS) was added and incubated on the cells at 25° C. for 60 min. The cells were rinsed with PBS and a secondary antibody (goat anti-mouse IgG) was added to the cells and incubated for 30 rain at 25° C. Then peroxidase reagent and chromogen reagent were added according to the manufacturers' specifications. Immunostaining for OP, OC, ON, BSP, and type I collagen were performed in the same manner except that day 8 (postconfluent) cells were fixed in absolute ethanol, blocking was done with 10% (v/v) FBS in PBS, and the secondary antibody was goat anti-rabbit IgG.

cAMP Quantitation

The hFOB cells were cultured in 6 well dishes to confluence (approximately $5 \times 10^5$ cells/well) at 33.5° C. in DMEM/F12 media with 10% (v/v) FBS, then the culture media was replaced and the cells were incubated at 39.5° C. for 48 hrs. The cells were pretreated with 1 mM isobutylmethylxanthine (IMBX) for 2 min. The cells were then treated with either 1–34 PTH (1–100 nM), $PGE_2$, or forskolin (10 µM) for 10 min. The media were removed from the cells and the cells were rinsed immediately with cold (4° C.) PBS, scraped from the tissue culture dish in cold (–20° C.) 70% (v/v) ethanol, transferred to 1.5 ml microcentrifuge tubes, and sonicated on ice. The cell lysate was lyophilized in a speed vac concentrator and redissolved in 0.25 ml of Tris-EDTA buffer (50 mM Tris, pH 7.5, 4 mM EDTA). A portion (20–50 µl) of each lysate was mixed with 50 µl $^3$H-cAMP and 100 µl cAMP-binding protein solution and incubated at 4° C. for 120 min. The binding reaction was then mixed with 100 µl activated dextran-coated charcoal and centrifuged at 12,000 ×g for 5 min. A portion (200 µl) of the supernatant was then mixed with scintillation cocktail for quantitation of $^3$H.

Staining of Mineralized Matrix

Postconfluent hFOB cells were fixed in 1% (w/v) paraformaldehyde in Tris buffered saline (TBS=20 mM Tris, pH 7.4, 0.15 M NaCl) and rinsed with TBS. The cells were then stained by the von Kossa procedure as modified by Schenk et al. in *Methods of Calcified Tissue Preparation*, G. R. Dickson, eds. (Elsevier), 1–4 (1984), which is incorporated herein by reference. Briefly, the cells were treated with 5% (w/v) silver nitrate in the dark for 15 min. The cells were then rinsed with distilled water, subjected to ultraviolet light for 5 min, treated with sodium carbonate/formaldehyde solution for 2 min, and finally treated with Farmer's reducer as described in R. K. Schenk et al. for 30 sec.

Alkaline Phosphatase and Osteocalcin Assays

The hFOB cells were cultured in 6 well dishes to confluence in DMEM/F12 media with 10% (v/v) FBS at 33.5° C., then rinsed with about 3 ml serum-free media twice. The media was replaced with differentiation media (DMEM/F12 with 0.2% (v/v) charcoal-stripped FBS (csFBS), 100 µg/ml ascorbic acid, and $10^{-8}$ menadione) and the cells were incubated at the desired temperature for 24 hrs. The media was replaced again with differentiation media and the cells were treated with various doses of 1,25-$(OH)_2D_3$ or ethanol vehicle for 48 hrs. The media was removed and utilized for osteocalcin assays while the AP reaction was initiated by rinsing the cells twice with PBS and adding 0.5 ml of alkaline lysis buffer (0.75 M 2-Amino-2-methyl-1-propanol, pH 10.3) containing p-nitrophenol phosphate substrate (2 mg/ml), and incubating at 37° C. for 30 min. The reaction solution was mixed with an equal volume of 50 mM NaOH, then diluted 1:40 with 20 mM NaOH. The absorbance at 410 nm was determined and compared to p-nitrophenol standards. A portion of the reaction solution was used to determine total protein concentration by the Bradford method, as disclosed by M. M. Bradford, *Anal. Biochem.*, 72, 248 (1976), which is incorporated herein by reference.

A portion of conditioned media (400 µl) or media plus known OC standards (provided in kit) were mixed with a $^{125}$I-labelled antibody to human osteocalcin (anti-OC) and a plastic bead coated with the anti-OC antibody. These mixtures were incubated 18–24 hrs at 25° C., then the beads were rinsed with wash buffer as specified by the manufacturer in the osteocalcin RIA kit purchased from Immutopics. Briefly, the binding reaction buffer was removed and washed three times with 2 ml each time of a wash buffer. The rinsed beads were put into scintillation cocktail for quantitation of $^{125}$I. The control and treated samples were compared to the standard curve for quantitation of OC.

Results

Primary cultures isolated from fetal tissue were transfected with a gene coding for a temperature sensitive mutant (tsA58) of SV40 large T antigen, along with a gene coding for neomycin (G418) resistance. Individual neomycin resistant colonies were screened for alkaline phosphatase (AP) specific staining. The clone with the highest AP level, hFOB 1.19, was examined further for other osteoblast phenotypic markers. Thymidine incorporation experiments indicated that incubation of hFOB 1.19 cells at a permissive temperature of 33.5° C. resulted in rapid cell division, whereas little or no cell division occurred at a restrictive temperature of 39.5° C. Measurement of AP activity in hFOB cell extracts indicated that cells cultured at 39.5° C. had 2–3 fold higher levels of AP than cells cultured at 33.5° C. Further, AP activity increased in a dose-dependant manner following treatment with 1,25-Dihydroxyvitamin $D_3$ (1,25-$(OH)_2D_3$) when cultured at either temperature. Similarly, radioimmunoassay (RIA) analyses showed that the level of osteocalcin secreted from 1,25-$(OH)_2D_3$-treated hFOB 1.19 cells was 10 fold higher when the cells were cultured at 39.5° C. compared to cells cultured at 33.5° C. In addition, osteocalcin levels in hFOB 1.19-conditioned media increased in a dose-dependant manner following 1,25-$(OH)_2D_3$ treatment at both 39.5° C. and 33.5° C. incubations. Treatment of hFOB 1.19 cells with 1–34 parathyroid hormone (PTH) at 39.5° C. resulted in a 3 fold increase in cAMP levels as measured by RIA. Upon reaching confluence, hFOB 1.19 cultures went through programmed differentiation and formed mineralized nodules as observed by von Kossa staining. Further, immunostaining of postconfluent, differentiated hFOB cells showed that high levels of osteocalcin, osteopontin, osteonectin, bone sialoprotein, and type I collagen were expressed.

Temperature Control of hFOB Cell Proliferation

Since hFOB 1.19 cells were transfected with a temperature sensitive mutant tsA58 of SV40 large T antigen, the effect of incubation temperature on hFOB 1.19 cell proliferation was examined. The rate of thymidine incorporation by hFOB 1.19 cells cultured at various temperatures was measured to indirectly reflect the rate of hFOB 1.19 cell division. These data (see FIG. 1) indicate hFOB cells cultured at the permissive temperature of 33.5° C. proliferated rapidly with a doubling time of about 36 hrs. Similarly, microscopic inspection indicated an increase in cell number from less than about 20% confluence to greater than about 80% confluence during the time course. In contrast, hFOB 1.19 cells cultured at the restrictive temperature of 39.5° C. did not appear to proliferate during the four day time course, whereas cells cultured at 38.0° C. proliferated very slowly, with a doubling time of greater than 96 hrs. However, when the cells were switched back to 33.5° C. after 24 hrs at 39.5° C., proliferation resumed and attained a rate similar to that observed with cells grown continuously at 33.5° C.

Karyotype Analysis

In order to characterize the chromosomal makeup of the hFOB 1.19 cells, karyotype analysis was performed on passage 12 cells. The data from 100 metaphases indicate that 43% of the cells were diploid and 57% were tetraploid. Among a group of 12 diploid metaphases analyzed further, 7 were normal 46,XX and 5 were 44–46,XX with an 18q+ translocation. Chromosome polymorphism patterns were consistent with a clonal cell population. The hFOB 1.19 clone has been cultured at 33.5° C. up to passage 30 (approximately 100 population doublings) without crisis. At passage 32 to 34 the cells entered crisis and proliferation slowed considerably.

Expression of Osteoblast Phenotypic Markers and SV40 T Antigen

To determine whether hFOB 1.19 cells express proteins which are characteristic of the osteoblast phenotype and to confirm that the transfected SV40 large T antigen (T Ag) gene is expressed, immunostaining was performed with antibodies specific to osteopontin (OP), osteonectin (ON), osteocalcin (OC), bone sialoprotein (BSP), type I collagen, and T Ag. The results of these immunostaining experiments (see FIG. 2) showed that high levels of the differentiation markers OP, ON, OC, BSP, and type I collagen were expressed in postconfluent hFOB cells cultured at 33.5° C. In addition, high levels of T Ag were localized in the nuclei of hFOB cells.

Induction of cAMP Levels by PTH and PGE

Figure 3:
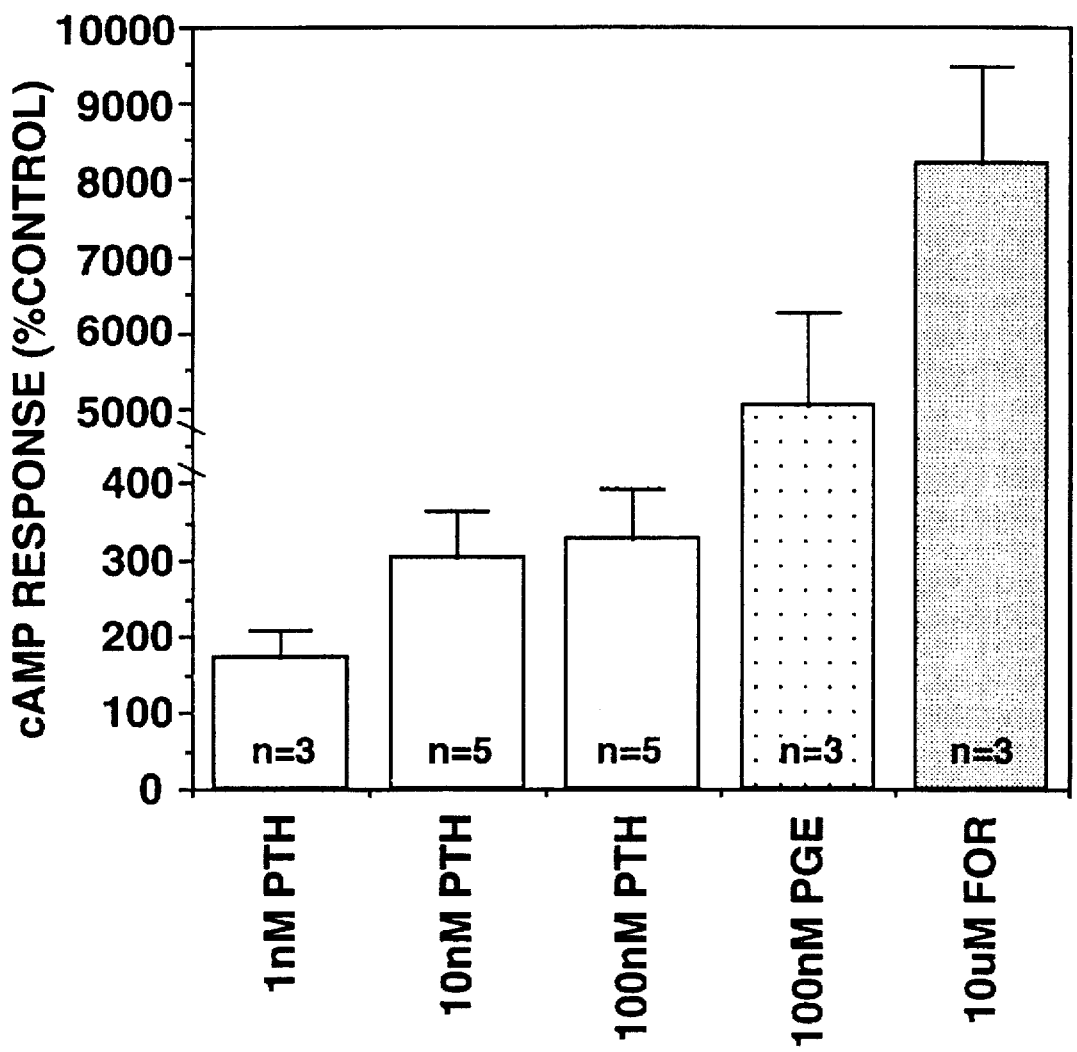
FIG. 3. Induction of cAMP levels in hFOB 1.19 cells by various agonists. Confluent hFOB 1.19 cells (at 39.5° C.) were pretreated with 1 mM IBMX for 2 min, then treated with the indicated dose of each agonist for 10 min. Quantitation of cAMP levels was then performed by RIA, and the amount of cAMP (pmoles/$10^5$ cells) for each agonist treatment was compared to control treatment (IBMX only) and expressed as a percentage (as denoted). Error bars=SEM (standard error of the mean), n=number of experiments (as denoted).
Figure 4A:
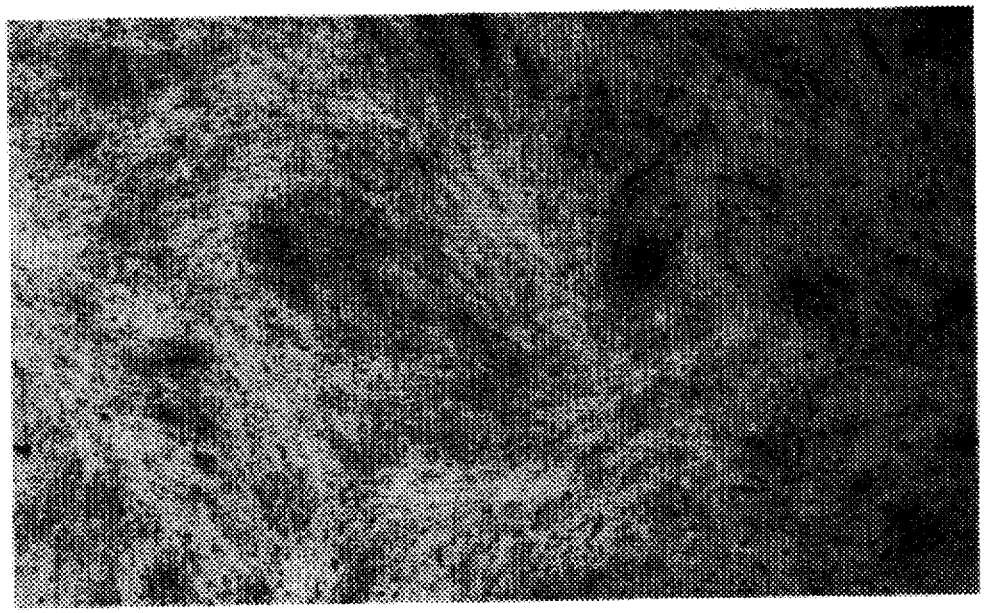
FIG. 4. Mineralization of the extracellular matrix by hFOB 1.19 cells. The hFOB cells were cultured at 33.5° C. past confluence (day 0), then stained by the von Kossa method to visualize mineralization of the extracellular matrix on the following days: (A) day 2; (B) day 4; (C) day 6; (D) day 8; and (E) day 10. Darkly stained areas are nodules with mineralized matrix (25× magnification).
Figure 4B:
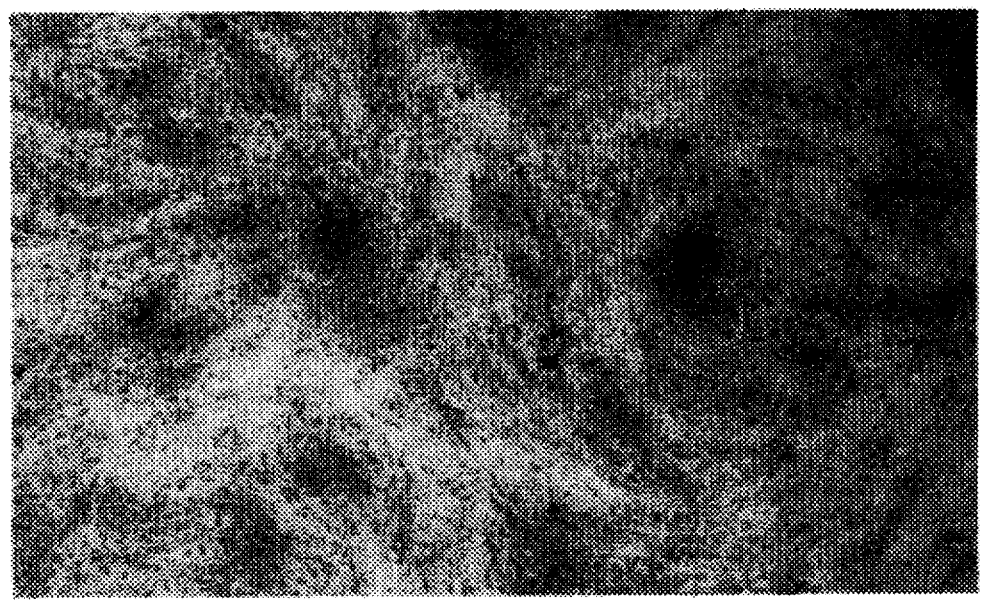
Figure 4C:
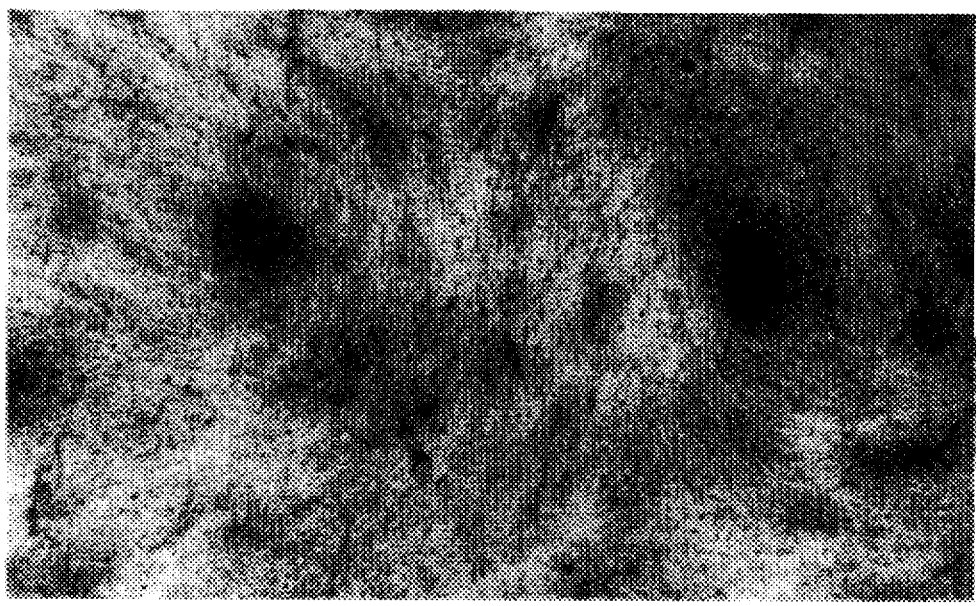
Figure 4D:
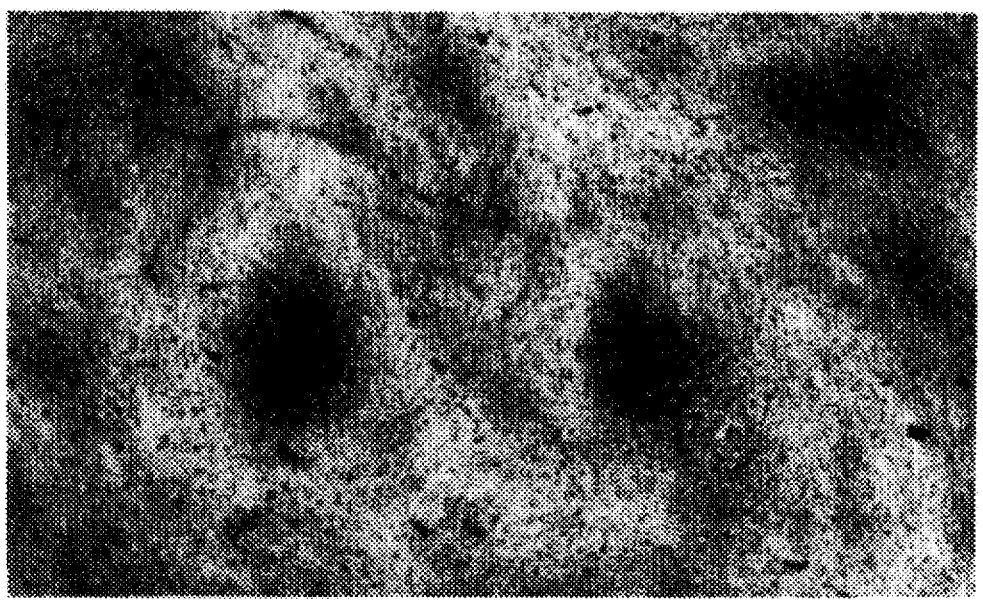
Figure 4E:
Figure 5A:
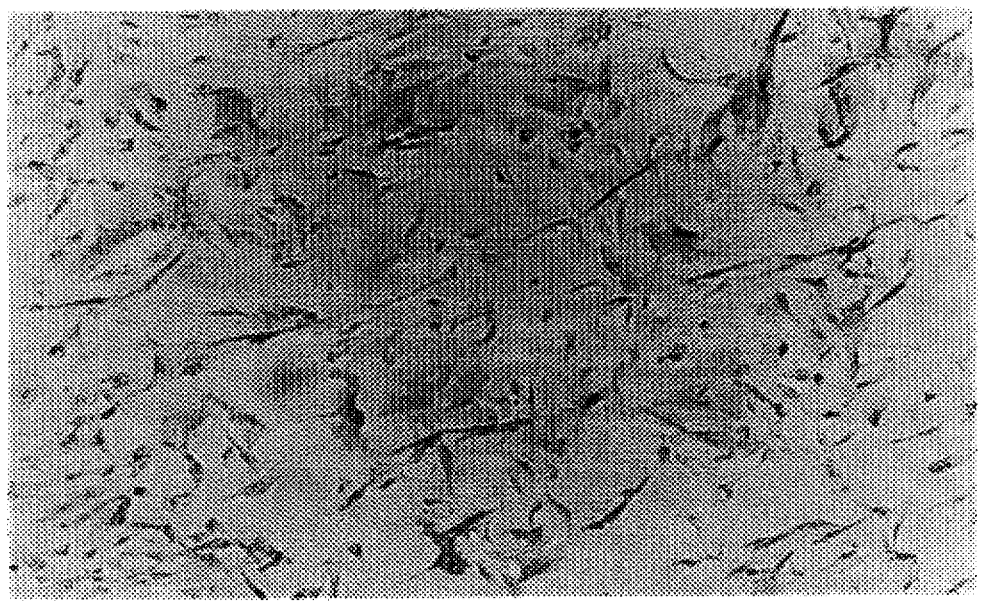
FIG. 5. Regulation of alkaline phosphatase (AP) activity in hFOB 1.19 cells. Subconfluent (A and C) or confluent (B and D) hFOB cells were incubated at either 33.5° C. (A and B) or 39.5° C. (C and D) in differentiation media, then fixed and incubated with a substrate-based stain for AP activity in situ. Dark staining indicates high AP activity (200× magnification). (E) Confluent hFOB cells were incubated at the indicated temperatures in differentiation media for 24 hrs, then treated for 48 hrs with the indicated doses of 1,25-dihydroxy vitamin $D_3$ (1,25-$(OH)_2D_3$), or ethanol vehicle (control) at the indicated temperatures. AP activity in cell extracts was then measured using the p-nitrophenol phosphate assay and normalized to total protein. Units= μmoles p-nitrophenol/hr at 37° C. Error bars=1 standard deviation, n=6 experiments. **=P<0.01 vs control, $=P<0.001 39.5° C. vs 33.5° C., two-tailed student's paired T test.
Figure 5B:
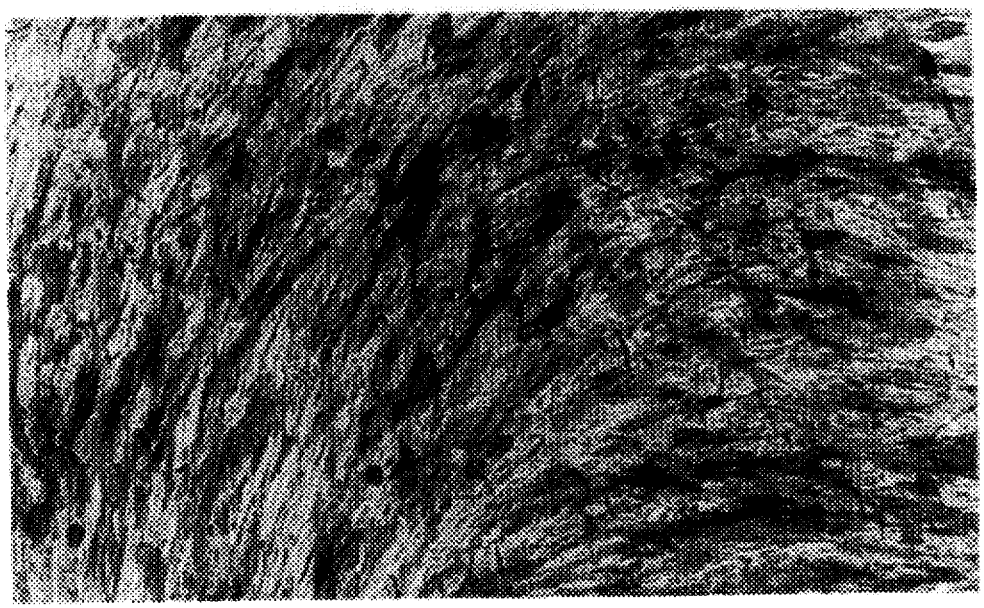
Figure 5C:
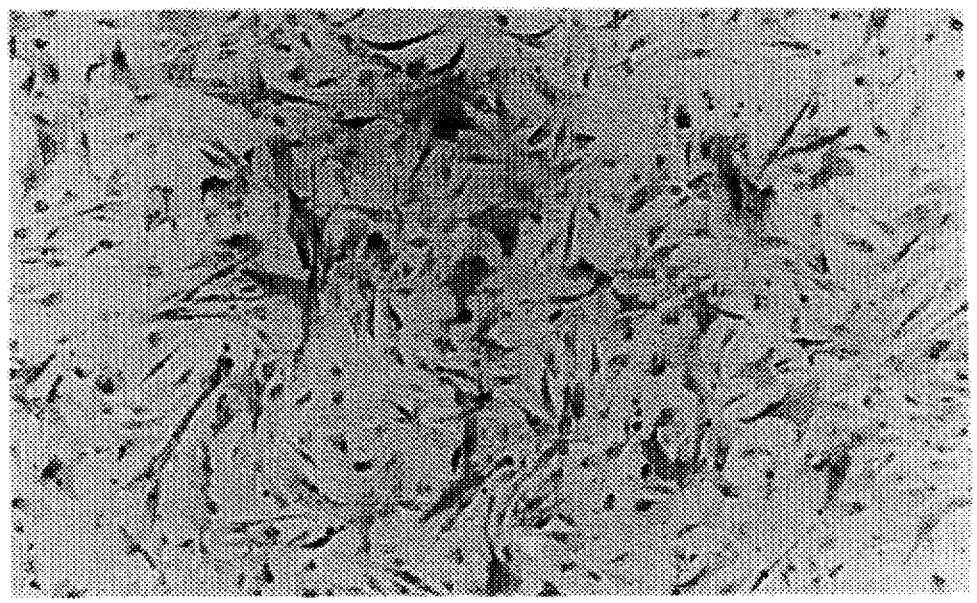
Figure 5D:
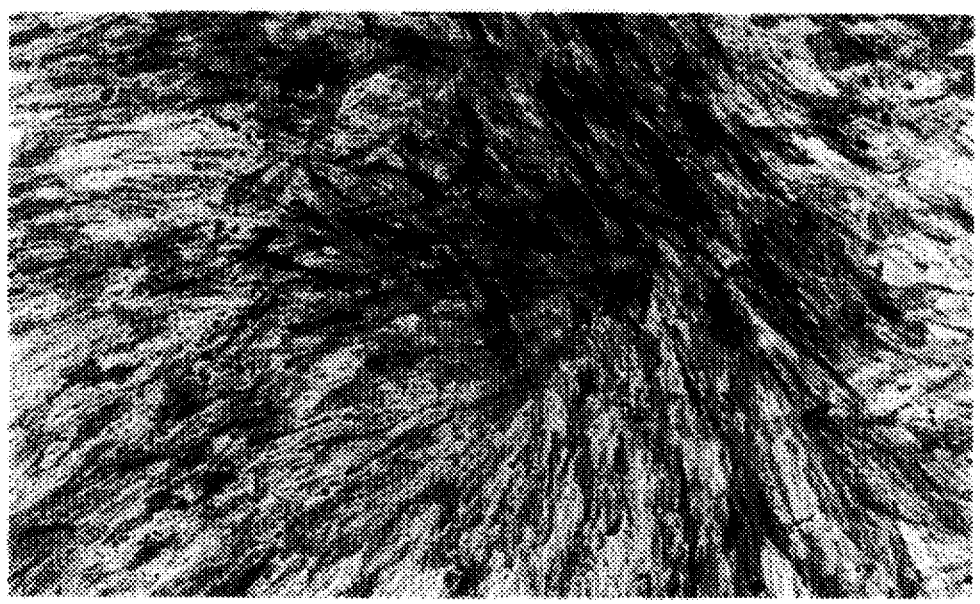
Figure 5E:
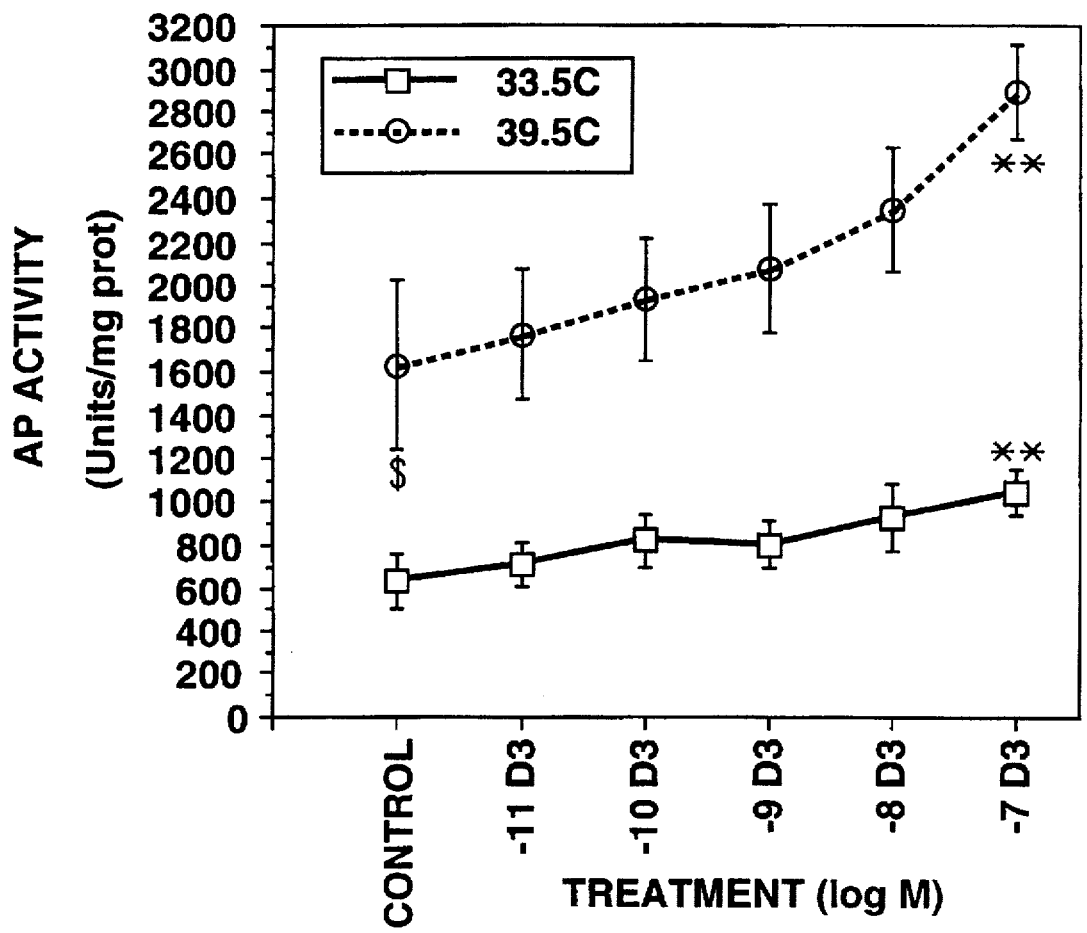

Since cAMP levels have been shown previously to be affected by PTH and $PGE_2$ in other osteoblastic cell lines, these cAMP agonists were examined for their activity in hFOB 1.19 cells by radioimmunoassay. The data (see FIG. 3) indicate that cAMP levels increased more than 3 fold when hFOB 1.19 cells were treated with 10 nM or 100 nM PTH, but increased less than 2 fold when treated with 1 nM PTH. Dramatic increases in cAMP levels were observed following treatment with 100 nM $PGE_2$ (>50 fold increase) or with the known agonist 10 μM forskolin (>80 fold increase).

Formation of Mineralized Nodules

Many osteoblastic cell lines have been shown to form mineralized nodules during the processes of cell differentiation and matrix mineralization. Upon culturing hFOB 1.19 cells beyond confluency (day 0) at 33.5° C., formation of mineralized nodules occurred gradually until nodules were clearly visible by day 8–10. Nodule formation was also observed in postconfluent cells cultured at 39.5° C. To visualize calcium deposition within the nodules, the cells were stained by the von Kossa procedure and examined under light microscopy. These data (see FIG. 4) showed that calcium deposition within the nodules was easily detectable by day 4–6 and became extensive by day 8–10 post confluency. Interestingly, nodule formation and calcium deposition were extensive even without the addition of β-glycerophosphate or high doses of glucocorticoids to the culture media.

Regulation of Alkaline Phosphatase Activity

Since initial screenings of neomycin-resistant transfectants indicated that the highest level of AP was present in hFOB 1.19 cells, the regulation of AP in this clone was examined by performing substrate-based staining and standard enzyme assays under various culturing conditions. To determine whether AP activity within hFOB 1.19 cells changes upon reaching confluency or changes by incubation temperature, substrate-based staining was performed. These data (see FIG. 5, panels A–D) indicated that AP activity increased dramatically upon reaching confluency at either incubation temperature (33.5° C. or 39.5° C.). This reflects a change in the differentiation state of hFOB 1.19 cells to a more mature phenotype. The amount of AP-specific staining was clearly much higher in confluent cells (FIG. 5, panels B and D) than subconfluent cells (panels A and C). Although there appeared to be a slightly higher level of AP activity in hFOB 1.19 cells cultured at 39.5° C. (panels C and D) compared to cells cultured at 33.5° C. (panels A and B), this difference may be at the limit of sensitivity for this assay. In order to quantitate changes in AP activity resulting from modification of the incubation temperature or by the addition of $1,25\text{-}(OH)_2D_3$ to the media, standard enzyme assays with hFOB 1.19 cell extracts were performed. These data (see FIG. 5, panel E) showed that AP activity was 2–3 fold higher in hFOB 1.19 cells cultured at 39.5° C. compared to cells cultured at 33.5° C. In addition, treatment of hFOB 1.19 cells with $1,25\text{-}(OH)_2D_3$ resulted in a dose-dependant increase in AP activity in cells cultured at either temperature (33.5° C. or 39.5° C). This effect of $1,25\text{-}(OH)_2D_3$, was relatively modest as the highest dose (100 nM) produced less than a 2 fold increase in AP activity.

Regulation of Osteocalcin Expression

Figure 6:
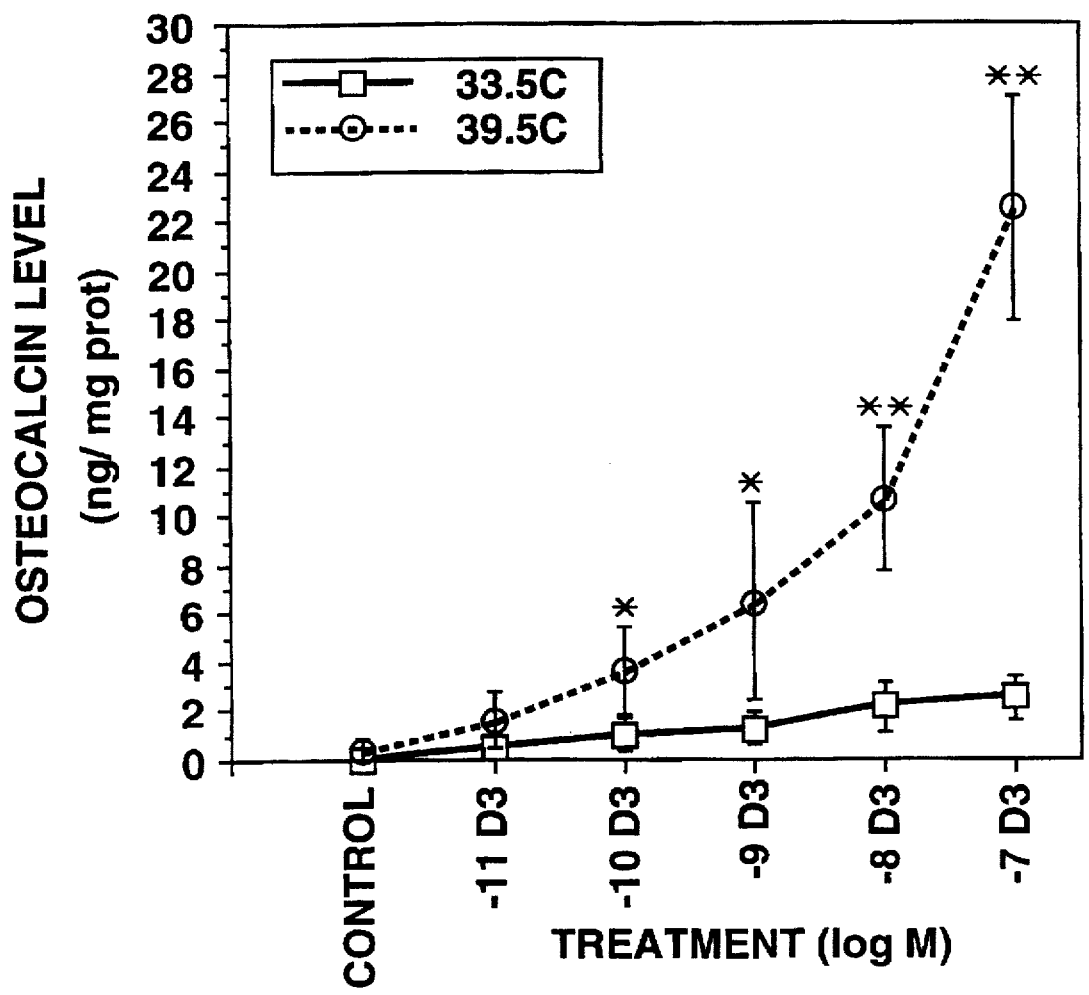
FIG. 6. Regulation of osteocalcin expression in hFOB 1.19 cells. Confluent hFOB 1.19 cells were incubated at the indicated temperatures in differentiation media for 24 hrs, then treated for 48 hrs with the indicated doses of 1,25-dihydroxy vitamin $D_3$ (1,25-$(OH)_2D_3$), or ethanol vehicle (control) at the indicated temperatures. OC levels in hFOB-conditioned media were measured by RIA using a $^{125}I$-labelled antibody to human OC and normalized to total protein in cell extracts. Error bars=1 standard deviation, n=6 experiments. *=P<0.05 39.5° C. vs 33.5° C., **=P<0.01 39.5° C. vs 33.5° C., two-tailed student's paired T test.

To determine whether hFOB 1.19 cells secrete the osteoblast specific protein osteocalcin (OC) and to determine whether OC production is regulated by $1,25\text{-}(OH)_2D_3$ or by incubation temperature, radioimmunoassays with hFOB 1.19-conditioned media were performed. These data (see FIG. 6) indicated that OC levels in hFOB 1.19-conditioned media was near or below the levels of detection without $1,25\text{-}(OH)_2D_3$ treatment when the cells are cultured at either temperature (33.5° C. or 39.5° C.). However, treatment of hFOB 1.19 cells with $1,25\text{-}(OH)_2D_3$ resulted in a dramatic increase in OC levels in a dose-dependant manner. Treatment with doses of $1,25\text{-}(OH)_2D_3$ as low as 0.1 nM resulted in a notable increase in OC levels, particularly when the cells were cultured at 39.5° C. Similarly, treatment with higher doses of $1,25\text{-}(OH)_2D_3$ resulted in correspondingly higher levels of OC. Interestingly, the effect of $1,25\text{-}(OH)_2D_3$ on OC levels was more pronounced when the hFOB 1.19 cells were cultured at 39.5° C. In fact, when the cells were treated with 100 nM $1,25\text{-}(OH)_2D_3$, the level of OC secreted by cells cultured at 39.5° C. was 10 fold higher than cells cultured at 33.5° C.

Deposit of Cells

The immortalized human fetal cells hFOB 1.19 have been deposited with the American Type Culture Collection (ATCC), 12301 Parklawn Drive, Rockville, Md. 20852 USA on Jun. 4, 1993 and assigned accession number ATCC CRL 11372. The complete taxonomic description is human fetal osteoblast cell line hFOB 1.19.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An immortalized normal human fetal osteoblastic cell which expresses a temperature sensitive mutant of simian virus 40 large T protein antigen.

2. The immortalized normal human fetal osteoblastic cell of claim 1 wherein the cell is part of a homogeneous population.

3. The immortalized normal human fetal osteoblastic cell of claim 2 wherein the homogeneous population is a clonal population.

4. The immortalized normal human fetal osteoblastic cell of claim 1 which is nontumorigenic.

5. The immortalized normal human fetal osteoblastic cell of claim 1 wherein the T antigen is inactivated at a restrictive temperature.

6. The immortalized normal human fetal osteoblastic cell of claim 5 wherein the T antigen is either cycled between an inactive and an active state or not cycled between an inactive and an active state.

7. The immortalized normal human fetal osteoblastic cell of claim 1 which undergoes osteoblastic differentiation.

8. An immortalized normal human fetal osteoblastic cell having the identifying characteristics of ATCC CRL 11372.

9. An immortalized normal human fetal osteoblastic cell prepared by a process comprising transfecting a human fetal bone cell with a gene coding for a temperature sensitive mutant of simian virus 40 large T antigen.

10. The immortalized normal human fetal osteoblastic cell of claim 9 wherein the process further comprises transfecting the cell with a gene coding for a selectable marker.

11. An immortalized normal human fetal osteoblastic cell prepared by a process comprising transfecting a human fetal bone cell with expression vector pUCSVtsA58.

12. The immortalized normal human fetal osteoblastic cell of claim 11 wherein the process further comprises transfecting the human fetal bone cell with expression vector pSV2neo.

13. A method of preparing an immortalized normal human fetal osteoblastic cell comprising:
   (a) isolating a bone cell from human fetal tissue; and
   (b) transfecting the isolated human fetal tissue cell with an expression vector comprising a gene coding for a temperature sensitive mutant of simian virus 40 large T antigen to yield said immortalized normal human fetal osteoblastic cell which expresses said antigen.

14. The method of claim 13 wherein the expression vector is a plasmid expression vector.

15. The method of claim 13 further comprising a step of transfecting the isolated human fetal bone cell with a selectable marker gene.

* * * * *